(12) United States Patent
Han et al.

(10) Patent No.: US 11,535,674 B2
(45) Date of Patent: *Dec. 27, 2022

(54) BIVALENT BISPECIFIC ANTIBODY HYBRID PROTEIN EXPRESSION AND PREPARATION METHODS

(71) Applicants: SHANGHAI JIAO TONG UNIVERSITY, Shanghai (CN); JECHO LABORATORIES INC., Frederick, MD (US); JECHO BIOPHARMACEUTICALS CO LTD., Tianjin (CN)

(72) Inventors: Lei Han, Shanghai (CN); Jianwei Zhu, Shanghai (CN); Junsheng Chen, Shanghai (CN); Kai Ding, Shanghai (CN); Yueqing Xie, Shanghai (CN); Hua Jiang, Shanghai (CN); Huili Lu, Shanghai (CN); Baohong Zhang, Shanghai (CN); Lei Zhang, Shanghai (CN)

(73) Assignees: SHANGHAI JIAO TONG UNIVERSITY, Shanghai (CN); JECHO LABORATORIES INC., Frederick, MD (US); JECHO BIOPHARMACEUTICALS CO LTD., Tianjin (CN)

(*) Notice: Subject to any disclaimer, the term of this patent is extended or adjusted under 35 U.S.C. 154(b) by 6 days.

This patent is subject to a terminal disclaimer.

(21) Appl. No.: 16/079,003

(22) PCT Filed: Dec. 16, 2016

(86) PCT No.: PCT/CN2016/110290
§ 371 (c)(1),
(2) Date: Aug. 22, 2018

(87) PCT Pub. No.: WO2017/143838
PCT Pub. Date: Aug. 31, 2017

(65) Prior Publication Data
US 2019/0062434 A1   Feb. 28, 2019

(51) Int. Cl.
*C12N 15/62* (2006.01)
*C07K 16/28* (2006.01)
*C07K 16/46* (2006.01)
*C07K 16/06* (2006.01)

(52) U.S. Cl.
CPC ........ *C07K 16/2863* (2013.01); *C07K 16/065* (2013.01); *C07K 16/46* (2013.01); *C12N 15/62* (2013.01); *C07K 2317/31* (2013.01); *C07K 2317/35* (2013.01); *C07K 2317/51* (2013.01); *C07K 2317/524* (2013.01); *C07K 2317/92* (2013.01); *C07K 2319/20* (2013.01); *C07K 2319/92* (2013.01)

(58) Field of Classification Search
CPC ............ C07K 2319/92; C07K 2317/53; C07K 2317/31; C07K 16/065; C12N 15/62
USPC ..................... 424/133.1; 530/387.3
See application file for complete search history.

(56) References Cited

U.S. PATENT DOCUMENTS

| | | | |
|---|---|---|---|
| 7,405,276 B2* | 7/2008 | Himawan | A61P 31/18 530/387.3 |
| 9,567,609 B2* | 2/2017 | Paschon | A61P 35/00 |
| 9,796,967 B2* | 10/2017 | Ma | C07K 1/22 |
| 10,072,066 B2* | 9/2018 | Liu | A61K 35/28 |
| 10,081,661 B2* | 9/2018 | Miller | A61P 7/04 |
| 10,323,235 B2* | 6/2019 | Ma | C07K 1/22 |
| 10,538,787 B2* | 1/2020 | Paschon | A61P 43/00 |
| 2003/0157091 A1* | 8/2003 | Hoogenboom | C07K 16/00 424/130.1 |
| 2015/0197734 A1* | 7/2015 | Ma | C07K 14/4702 435/196 |
| 2018/0346891 A1* | 12/2018 | Ma | C12N 9/16 |
| 2020/0317819 A1* | 10/2020 | Zhu | A61K 47/6849 |

FOREIGN PATENT DOCUMENTS

| | | |
|---|---|---|
| CN | 106397599 | 2/2017 |
| WO | 02/46208 | 6/2002 |
| WO | 2004/101739 | 11/2004 |
| WO | WO 2013/045632 | * 4/2013 |

OTHER PUBLICATIONS

Shibuya et al. (Protein Eng Des Sel. Jan. 2017;30(1):15-21. Epub Nov. 23, 2016).*
Han et al. (Sci Rep. Aug. 21, 2017;7(1):8360. doi: 10.1038/s41598-017-08641-3).*
Han et al. (Methods. Feb. 1, 2019;154:32-37. doi: 10.1016/j.ymeth.2018.10.001. Epub Oct. 9, 2018).*
Hemmi et al. (Biochem Biophys Res Commun. Feb. 26, 2020;523(1):72-77. doi: 10.1016/j.bbrc.2019.12.018. Epub Dec. 9, 2019).*
Hofmann et al. (MAbs. Jan.-Dec. 2020;12(1):1731938. doi: 10.1080/19420862.2020.1731938).*
Saleh et al. (The Chemical Record, vol. 6, 183-193 (2006)).*
Ozawa et al (Nat. Biotech. 21: 287-293 (Mar. 2003), Published online Feb. 10, 2003).*
Zettler et al (FEBS Letters 583 (2009) 909-914).*
International Search Report for corresponding PCT/CN2016/110290.
Written Opinion and notifications for corresponding PCT/CN2016/110290.

(Continued)

*Primary Examiner* — Lynn A Bristol
(74) *Attorney, Agent, or Firm* — Oblon, McClelland, Maier & Neustadt, L.L.P.

(57) ABSTRACT

The present disclosure discloses a method for expressing and preparing a bivalent bispecific antibody. In the present disclosure, each portion of a bivalent bispecific antibody and an immune hybrid protein thereof is respectively expressed in a suitable prokaryotic or eukaryotic cell system, separated and purified by high-performance affinity chromatography, and then spliced in vitro by trans-splicing reaction mediated by an intein, to prepare the bivalent specific antibody and an immune hybrid protein thereof.

10 Claims, 10 Drawing Sheets

(56) References Cited

OTHER PUBLICATIONS

Ridgway, J.B.B. et al.,—Knobs-into-holes' engineering of antibody CH3 domains for heavy chain heterodimerization, Protein Engineering, vol. 9, No. 7, Dec. 31, 1996 (Dec. 31, 1996), p. 617, right-hand column "Materials and methods".

Lewis, S.M. et al., "Generation of bispecific IgG antibodies by structure-based design of an orthogonal Fab interface", Nature Biotechnology, vol. 32, No. 2, Jan. 26, 2014 (Jan. 26, 2014), pp. 191-198.

Spiess, C. et al., "Bispecific antibodies with natural architecture produced by co-culture of bacteria expressing two distinct half-antibodies" Nature Biotechnology, vol. 31, No. 8, Jul. 7, 2013 (Jul. 7, 2013), pp. 753-758.

Li, Geng et al., "Application of Bispecific Antibody Drugs", Current Biotechnology, vol. 5, No. 6, Dec. 31, 2015 (Dec. 31, 2015), pp. 420-424.

Pharmaceutical Biotechnology, 2007, 14 (6), pp. 445-450 w/English Abstract.

Merchant, et al., Nature Biotechnology, vol. 16, Jul. 1998, "An efficient route to human bispecific IgG".

Sydor, et al., "Establishment of Intein-Mediated Protein Ligation under Denaturing Conditions: C-Terminal Labeling of a Single-Chain Antibody for Biochip Screening", Botconjugate Chem. 2002, 13, 707-712.

Vila-Perello, et al., "Streamlined Expressed Protein Ligation Using Split Inteins", Journal of the American Chemical Society, 2013, (135), 286-292.

Kline, et al., "Methods to Make Homogenous Antibody Drug Conjugates" Pharm Res (2015) 32:3480-3493.

Mohlmann et, al., "Site-specific modification of ED-B-targeting antibody using intein-fusion technology", Mohlmann et al., BMC Biotechnology, 2011, 11:76.

Han, et al., "Efficient generation of bispecific IgG antibodies by split intein mediated protein trans-splicing system", Scientific Reports, 7:8360 (2017), 10 pages.

Shibuya, et al., "Generation of camelid VHH bispecific constructs via in-cell intein-mediated protein trans-splicing", Protein Engineering, Design & Selection, 2017, vol. 30, No. 1, pp. 15-21.

Han, et al., "Naturally split intein Npu DnaE, mediated rapid generation of bispecific IgG antibodies", Methods, 154, (2019) 32-37.

\* cited by examiner

BIVALENT BISPECIFIC ANTIBODY HYBRID PROTEIN EXPRESSION AND PREPARATION METHODS

CROSS-REFERENCE TO RELATED APPLICATIONS

This application is a national stage application of PCT Application No. PCT/CN2016/110290. This Application claims priority from PCT Application No. PCT/CN2016/110290, filed Dec. 16, 2016, and CN Application No. 201610100217.9, filed Feb. 23, 2016, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the invention described herein. All references cited and discussed in this specification are incorporated herein by reference in their entireties and to the same extent as if each reference was individually incorporated by reference.

TECHNICAL FIELD

The present disclosure relates to the field of biological technologies, and particularly to a method for expressing and preparing a hybrid proteins of bivalent bispecific antibody.

BACKGROUND

A bispecific antibody refers to an antibody molecule that can recognize two antigens or two epitopes simultaneously, such as bispecific or multi-specific antibodies capable of binding two or more antigens known in the art, which can be obtained in eukaryotic expression systems or in prokaryotic expression systems through cell hybridization, chemical modification, and genetic recombination, etc.

Pharmacological studies have revealed that most of the complex diseases involve a variety of disease-related signaling pathways. For example, tumor necrosis factor (TNF), interleukin-6 and other pro-inflammatory cytokines simultaneously mediate immune inflammatory diseases, and the proliferation of tumor cells is often caused by abnormal upregulation of multiple growth factor receptors. Blockage of a single signaling pathway is usually limited in efficacy and is prone to cause the development of resistance. In the treatment of tumors, the expression of MHC on the surface of most cancer cells is down-regulated or even absent, causing escaping from immune killing. Bifunctional bispecific antibodies can simultaneously bind immune cells, and tumor cells, to redirect immune cells to tumors. Therefore, the development of bispecific antibodies and analogues thereof capable of simultaneously binding two different targets has long been an important area in the development of new structural antibodies.

An important mechanism of action of bispecific antibodies is to mediate T cell killing. In recent years, with the deep insight into the immune escape mechanism of cancer cells and the rise of cancer immunotherapy, the research of antibody drugs for activating T cells has received much attention. It is generally believed that effective activation of T cells requires dual signals. The first signal is from the binding of the MHC-antigen complex on the antigen-presenting cell to the T cell receptor TCR-CD3, and the second signal is a non-antigen-specific costimulatory signal produced upon interaction of the T cells with a co-stimulatory molecule expressed by the antigen-presenting cells. The expression of MHC on the surface of most cancer cells is down-regulated or even absent, causing escaping from immune killing. CD3× bispecific antibodies can bind to surface CD3 molecules on T cells and surface antigens on cancer cells, respectively, thereby shortening the distance between cytotoxic T cells (Tc or CTL) and cancer cells, and directing T cells to directly kill cancer cells, independent of the dual activation signals of T cells (Baeuerle. P A, Cancer Res. 69 (2009) 4941-4944). The unique activation pattern of T cells by CD3× bispecific antibodies is considered to be a major advantage in its mechanism of action.

Another important mechanism of action of bifunctional bispecific antibodies is the simultaneous binding to dual targets to block dual signaling pathways. The mechanism has found use in a wide range of applications, including cancer, autoimmune diseases, inhibition of blood vessel growth and anti-infective treatment. For example, the transmembrane tyrosine kinase receptor HER family plays an important regulatory role in cellular physiology and includes HER1 (erbB1, EGFR), HER2 (erbB2, NEU), HER3 (erbB3), HER4 (erbB4), and other members, which are abnormally highly expressed on the surface of many epithelial-derived solid tumor cells, and thus important targets for tumor targeted therapy. The antibodies that get available in market include Herceptin that binds to the HER2 D4 domain, Perjeta that binds to the HER2 D2 domain, and Erbitux that binds to HER1/EGFR, which are widely used in the clinical treatment of solid tumors such as breast cancer, stomach cancer and colorectal cancer. Studies have revealed that the homo- or heterodimers of the same or different members from the HER family activate the intracellular signals and promote the cell proliferation and tumor development. Herceptin blocks the homodimerization of the HER2 receptor, but not the heterodimerization of HER2 and other receptors. HER2 and HER3 are the most potent dimeric forms from the HER family that activate the initial oncogenic signaling. Perjeta capable of blocking this dimerization is clinically used in combination with Herceptin, and a better efficacy than that of a single antibody alone is achieved, indicating the clinical effect of dual target blockage (Kristjansdottir. K., Expert Opin biol Ther 10 (2010) 243-250).

Split intein is composed of an N-fragment of intein (In) and a C-fragment of intein (Ic). The gene expressing a precursor protein is split in two open reading frames. The split site is inside the intein sequence. The expression genes of the N-extein (En) and the In of the split intein form a fusion gene, and the fusion protein formed after translation is called an N precursor protein. The expression genes of the Ic of the split intein and the C-extein (Ec) form a fusion gene, and the fusion protein produced after translation is called a C precursor protein. The In or Ic of the split intein alone does not have a protein splicing function. However, after translation into a protein, the In in the N precursor protein and the Ic in the C precursor protein recognize and bind to each other by a non-covalent bond to form a functional intein, and thus can catalyze the protein trans-splicing to link two separated exteins (En, EC) with a peptide bond (Ozawa. T., Nat Biotechbol 21 (2003) 287-93).

Protein trans-splicing refers to a protein splicing reaction mediated by a split intein. In this type of splicing process, the In and Ic of the split intein first recognize and bind to each other by a non-covalent bond. After binding, the structure is properly folded, and the split intein with a re-constructed active center completes the protein splicing reaction following a typical protein splicing route, to link the extein at both sides (Saleh. L., Chemical Record 6 (2006) 183-193).

A wide variety of recombinant bispecific antibody formats have been developed in the recent past, for example, tetravalent bispecific antibodies by fusion of e.g. an IgG antibody format and single chain domains (see, for example, Coloma, M J, et al, Nature Biotech. 15 (1997) 159-163; WO 2001077342; and Morrison, S., L., Nature Biotech. 25 (2007) 1233-1234). Due to the large difference in structure from the natural antibodies, they cause a strong immune response and have a short half-life after entering the body.

Also several other new formats where the antibody core structure (IgA, IgD, IgE, IgG or IgM) is no longer retained small molecular antibodies such as dia-, tria- or tetrabodies, mini-bodies, several single chain formats (scFv, Bis-scFv), which are capable of binding two or more antigens, have been developed (Holliger, P., et al, Nature Biotech 23 (2005) 1126-1136; Fischer, N., and Léger, O., Pathobiology 74 (2007) 3-14; Shen, J., et al., J. Immunol. Methods 318 (2007) 65-74; and Wu, C., et al., Nature Biotech 25 (2007) 1290-1297). Although linking a core binding region of an antibody to a core binding protein of another antibody by a linker has advantages for the engineering of bispecific antibodies, problems may exist when they are used as a drug, which greatly limit the use thereof as a drug. Indeed, these foreign peptides might elicit an immune response against the linker itself or both the protein and the linker, causing cytokine storms. Furthermore, the flexible nature of these linkers makes them more prone to proteolytic cleavage, potentially leading to poor antibody stability, aggregation, increased immunogenicity, and short half-life. For example, blinatumomab from Amgen has a half-life of only 1.25 hours and needs be administered continuously by a syringe pump for 24 hours to achieve a therapeutic effect, thus greatly limiting the use (Bargou, R and Leo. E., Science 321 (2008)) 974-7). In addition one may want to retain effector functions of the antibody, such as complement-dependent cytotoxicity (CDC) or antibody dependent cellular cytotoxicity (ADCC) and extended half-life of binding to FcRn (Fc receptor) in vascular endothelium, which are mediated through the Fc region.

Thus ideally, one should aim at developing bispecific antibodies that are very similar in structure to naturally occurring antibodies (like IgA, IgD, IgE, IgG or IgM), and humanized bispecific antibodies and fully human bispecific antibodies with minimal deviation from human antibody sequences.

In 1983, bispecific antibodies that are very similar to natural antibodies were initially produced using the quadroma technology (Milstein, C and A. C. cuello, Nature, 305 (1983) 537-40). In the quadroma technology, two different murine monoclonal hybridoma cell lines are fused, and up to 10 different kinds of antibodies are produced after fusion, only one of which is the desired bispecific antibody. Due to the high similarity between the physical and chemical properties of the mis-paired products and the product of interest and the extremely low content of the product of interest, a sophisticated purification procedure is required (Morrison, S. L., Nature Biotech 25 (2007) 1233-1234). For example, the bispecific antibody Catumaxomab (Removab), which was marketed in Europe in 2009, causes a serious cytokine strom upon injection into the human body because the antibody is murine derived, which limits its prospects (Framton. J E., Drugs 72 (2012) 1399-410). Similarly, the mispairing of heavy chains and mispairing of light chains can still not be solved by the recombinant gene expression technology.

To solve the problem of mispairing of heavy chains, a "Knobs-into-Holes" theory is proposed, which aims at forcing the pairing of two different antibody heavy chains by introducing mutations into the CH3 domains of an antibody to modify the contact interface. On one CH3, bulky amino acids are mutated into amino acids with short side chains to create "holes". Conversely, amino acids with large side chains are introduced into the other CH3 domain, to create "knobs". By coexpressing two heavy chains and two light chains (which have to be appropriate for both heavy chains), high yields of heterodimer formation (knob-hole) versus homodimer formation ('hole-hole' or 'knob-knob') is observed (Ridgway, J. B., Protein Eng. 9 (1996) 617-621; and WO96/027011). Although this format appears very attractive, no data about use in clinic is currently available. One important constraint of this strategy is that the light chains of the two parent antibodies have to be identical to prevent mispairing of light chains and formation of impurity molecules. For the problem of mispairing of light chains, the binding specificity of an antibody is altered by mutation to form a "Two-in-One" bivalent bispecific antibody, such that the same specific binding domain of the antibody can bind to two antigens. The binding of such an antibody to each target is bivalent. Although desired effects can be obtained in linking and activating the target, a defect exists in blocking the effect of the antigens. This method requires a large amount of mutations and other genetic engineering means for each two antibody sequences, and is not a simple and general-purpose method (Bostrom, J., Science 323 (2009) 1610-1414; and Schaefer, G., Cancer Cell 20 (2011) 472-486). In addition, the problem of mispairing of light chains can be optimized by the crossmab (hybrid antibody) method. Exchange of some domains in the light chain and heavy chain of one Fab to form a crossmab (hybrid antibody) can be easily achieved. However, the hybrid antibody contains non-naturally occurring domain linked, losing the native antibody structure (Schaefer, W., Pro. Natl. Acad. Sci. USA 108 (2011) 1187-1192).

Genentech uses a method of co-culturing E. coli expressing two half-antibodies respectively to obtain a bispecific antibody. However, the antibody expressed by this method is not glycosylated, which affects the ADCC and half-life in blood, thus limiting the possibility for use as a drug (Spiess, C., Nature Biotechnol 31 (2013) 753-758). In order to produce a bispecific antibody having a structure similar to that of a naturally occurring antibody and containing glycosylation modifications, the problem of mispairing of heavy chains and mispairing of light chains is solved by undergoing structural analysis and site-directed mutagenesis at the interface of Fab, and by transient transfection of 293E cells by the "Knobs-into-Holes" technology, with which great improvements are made. However, in this method, a crystal model needs to be established for each antibody to design a suitable mutation screening site, such that the method is not universal for the construction of every bispecific antibody (Levis, S M, Nature Biotechnol 32 (2014) 191-198). In addition, in the cFAE "half-antibody exchange technology", half-antibodies are directed to recombine by introducing mutations in the CH3 region. An antibody is reduced into half antibodies by in vitro reduction, and then the half antibodies are oxidized into an intact antibody, thereby solving the problems of mispairing of heavy chains and mispairing of light chains. However, there will be 5% mispairing that cannot be solved, and the mis-paired products cannot be removed by purification. The presence of impurity components greatly limits the possibility of use of cFAE as a drug (Labrijin, A F, Nature protocol) (2014) 2045-2463).

Efforts have been made to establish a method for the production of bispecific antibodies which have no non-native domains, are highly structurally similar to natural antibodies (IgA, IgD, IgE, IgG or IgM), have an Fc domain and good structural integrity and stability, retain the complement-dependent cytotoxicity (CDC) or antibody dependent cellular cytotoxicity (ADCC), and have increased in vivo half-life of binding to FcRn (Fc receptor) and reduced immunogenicity. In the method, no linkers are introduced, so the stability of the antibody molecules is improved, and the immune response is reduced in vivo. The method can be used to produce humanized bispecific antibodies and fully human bispecific antibodies having a sequence close to human antibodies, thereby effectively reducing the immune response. The bispecific antibodies are produced in a mammalian cell expression system, have glycosylation modifications, have better biological functions, are more stable, and have long half-life in vivo. The mispairing of heavy chains is effectively avoided, and the mispairing rate can be reduced to 0%. The mispairing of light chains is effectively avoided, and the mispairing rate of light chains can be reduced to 0%. The method is a general-purpose method for constructing bispecific antibodies, has no limitations arising from antibody subtypes (IgG, IgA, IgM, IgD, IgE, IgM, and light chains κ and λ), does not require the design of different mutations depending on specific targets, and can be used to construct any bispecific antibodies.

Therefore, a heretofore unaddressed need exists in the art to address the aforementioned deficiencies and inadequacies.

SUMMARY

In view of the disadvantages of existing methods, an object of the present disclosure is to provide a novel method for expressing and preparing a hybrid proteins of bivalent bispecific antibody. In the present disclosure, a bispecific antibody is split into an antigen A binding portion and an antigen B binding portion for the first time, as shown (in FIGS. 2 and 3), which are expressed separately, and then ligated into a intact antibody by protein trans-splicing by a split intein. The portion A includes a light chain of an antibody A, an intact heavy chain of the antibody A, and an Fc chain having Ic fused to the N terminus. The B includes a light chain of an antibody B and a VH+CH1 chain of the antibody B having In fused to the C terminus The objects of the present disclosure are accomplished through the following technical solutions.

The present disclosure relates to a method for expressing and preparing a bivalent bispecific antibody. The bivalent bispecific antibody includes a first light chain and a first heavy chain of an antibody that specifically binds to a first antigen, and a second light chain and a second heavy chain of an antibody that specifically binds to a second antigen. The method includes the following steps:

S1: splitting an expressed sequence of the bivalent bispecific antibody, to obtain a portion A antibody and a portion B antibody, where the portion A antibody includes the first light chain, the first heavy chain, and an Fc chain of the second heavy chain having Ic fused to the N terminus; and the portion B antibody includes the second light chain and a VH+CH1 chain of the second heavy chain having In fused to the C terminus;

S2: constructing a mammalian cell expression vector by whole gene synthesis, to obtain a vector or vectors expressing the portion A antibody and a vector or vectors expressing the portion B antibody;

S3: transient transfection expressing mammalian cells with the vector expressing the portion A antibody as mediated by a transfection reagent, or a stable cell line expressing the portion A, to obtain the portion A antibody; and transient transfection expressing mammalian cells with the vector expressing the portion B antibody as mediated by a transfection reagent, or a stable cell line expressing the portion B, to obtain the portion B antibody; and S4: purifying the obtained portion A antibody and portion B antibody respectively, and subjecting the portion A antibody and the portion B antibody to protein trans-splicing in vitro, to obtain the bivalent bispecific antibody.

Preferably, a knob is formed at an interface of the CH3 domain in the first heavy chain, which can be located in a hole formed at an interface of the CH3 domain in the Fc chain of the second heavy chain having Ic fused to the N terminus.

Preferably, the threonine at position 366 in the CH3 domain of the first heavy chain is mutated to tryptophan to form the knob; and in the CH3 domain of the Fc chain of the second heavy chain having Ic fused to the N terminus, the threonine at position 366 is mutated to serine, the leucine at position 368 is mutated to alanine, and the tyrosine at position 407 is mutated to valine, to form the hole.

Preferably, the serine at position 354 in the CH3 domain of the first heavy chain is mutated to cysteine; and the tyrosine at position 349 in the CH3 domain of the Fc chain of the second heavy chain having Ic fused to the N terminus is mutated to cysteine.

Preferably, a hole is formed at an interface of the CH3 domain in the first heavy chain, in which a knob formed at an interface of the CH3 domain in the Fc chain of the second heavy chain having Ic fused to the N terminus can be located.

Preferably, in the CH3 domain of the first heavy chain, the threonine at position 366 is mutated to serine, the leucine at position 368 is mutated to alanine, and the tyrosine at position 407 is mutated to valine, to form the hole; and in the CH3 domain of the Fc chain of the second heavy chain having Ic fused to the N terminus, the threonine at position 366 is mutated to tryptophan, to form the knob.

Preferably, the tyrosine at position 349 in the CH3 domain of the first heavy chain is mutated to cysteine; and the serine at position 354 in the CH3 domain of the Fc chain of the second heavy chain having Ic fused to the N terminus is mutated to cysteine.

In the present disclosure, in order to improve the binding stability of the CH3 regions, the S (serine) at position 354 on the "knob" chain is mutated to C (cysteine), and the Y (tyrosine) at position 349 on the "hole" chain is mutated to C (cysteine), to enhance the stability between heavy chains by introducing a pair of inter-heavy chain disulfide bonds.

Preferably, in Step S2, the mammalian cell expression vector is constructed by whole-gene synthesis as follows. Specifically, whole-gene chemical synthesis is performed according to the designed split gene sequences. Restriction endonuclease cleavage sites are added at the two sides of the start codon and the stop codon by PCR. The genes are respectively inserted into a mammalian cell expression vector containing CMV promoter, the subclones are sequenced, and the plasmids are extracted.

Preferably, in Step S3, the transfection of the mammalian cells is transient transfection of 293-E, 293-F or CHO cells, and steady transfection of CHO cells.

Preferably, in Step S4, the in vitro trans-splicing is in vitro trans-splicing mediated by a split intein in the presence of a sulfhydryl compound.

Preferably, the in vitro trans-splicing occurs at a temperature of 4-37° C. and is continued for 5-120 min, and the concentration of the sulfhydryl compound is 0.05-2 mM.

Preferably, in Step S4, a step of purifying the spliced product by affinity chromatography is further included.

The present disclosure also relates to a method for expressing and preparing a bivalent bispecific antibody. The bivalent bispecific antibody is prepared following the method above and the method for expressing and preparing the immune hybrid protein includes the following steps:

B1: splitting an expressed sequence of the immune hybrid protein, to obtain a protein molecule, a portion A antibody, and a portion B antibody, where the portion A antibody includes a first light chain, a first heavy chain, and an Fc chain of a second heavy chain, in which the Fc chain has Ic fused to the N terminus; the portion B antibody includes a second light chain and a VH+CH1 chain of the second heavy chain, in which the VH+CH1 chain has In fused to the C terminus; and the protein molecule has In fused to one end, and at least one of the Fc chain of the second heavy chain and the Fc chain of the first heavy chain has Ic fused to the C terminus;

B2: constructing an eukaryotic or prokaryotic expression vector by whole-gene synthesis, and expressing and preparing the portion A antibody and the portion B antibody by transient transfection or steady transfection; and B3: after purification, subjecting the portion A antibody, the portion B antibody, and the protein molecule to Protein trans-splicing in vitro, to obtain the immune hybrid protein; and B4: subjecting the portion A antibody and the portion B antibody without purification, and the protein molecule to protein trans-splicing in vitro, to obtain the immune hybrid protein.

Compared with the prior art, the present disclosure has the following beneficial effects.

1) The bispecific antibodies have no non-native domains, are highly structurally similar to natural antibodies (IgA, IgD, IgE, IgG or IgM), have an Fc domain and good structural integrity and stability, retain the complement-dependent cytotoxicity (CDC) or antibody dependent cellular cytotoxicity (ADCC), and have increased in-vivo half-life of binding to FcRn (Fc receptor) and reduced immunogenicity.

2) No linkers are introduced, so the stability of the antibody molecules is improved, and the immune response is reduced in vivo.

3) The method can be used to produce humanized bispecific antibodies and fully human bispecific antibodies having a sequence close to human antibodies, thereby effectively reducing the immune response.

4) The antibodies are produced in a mammalian cell expression system, have glycosylation modifications, have better biological functions, are more stable, and have long half-life in vivo.

5) The mispairing of heavy chains is effectively avoided, and the mispairing rate can be reduced to 0%; and the mispairing of light chains is effectively avoided, and the mispairing rate of light chains can be reduced to 0%.

6) The method of the present disclosure is a general-purpose method for constructing bispecific antibodies, has no limitations arising from antibody subtypes (IgG, IgA, IgM, IgD, IgE, IgM, and light chains κ and λ), does not require the design of different mutations depending on specific targets, and can be used to construct any bispecific antibodies. 7) The method of the present disclosure can also be used to construct a bispecific antibody in which the Fc fragment is defective, for example, only a portion of the CH2 region in the Fc region is retained, or an intact CH2 region and a portion of the CH3 region are retained.

8) Moreover, the method of the present disclosure can also be used to construct a bispecific antibody in which the an Fab fragment remains, for example the portion A is Scfv, and the portion B is Fab; the portion A is Fab, and the portion B is Scfv; or the portion A is Scfv and the portion B is Scfv; and to construct a bispecific antibody retaining an intact Fc region or a defective Fc region.

9) The present disclosure is applicable to the construction of a small molecule antibody fragment of the type indicated by Group C and a small molecule fragment antibody of the type indicated by Group D in FIG. 5 by protein trans-splicing mediated by split intein.

BRIEF DESCRIPTION OF THE DRAWINGS

Other features, objects, and advantages of the present disclosure will become apparent upon reading the detailed description of non-limiting embodiments that follow with reference to the accompanying drawings.

FIG. 9 is a schematic view showing a heavy chain of a portion B antibody and IN;

DETAILED DESCRIPTION

Figure 1:
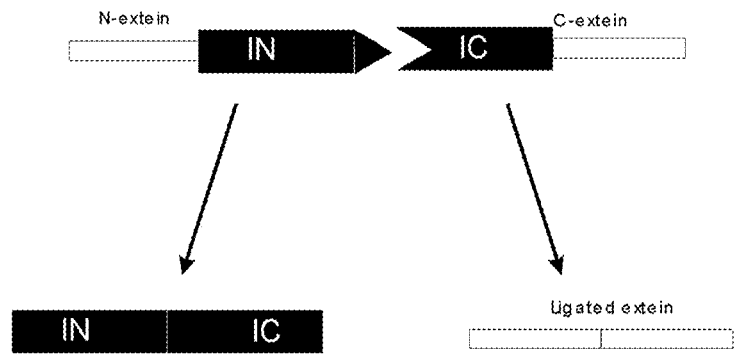
FIG. 1 is a schematic view showing the Protein trans-splicing mediated by a split intein.

Hereinafter, the present disclosure is described in detail by way of examples. The following examples are provided for better understanding of the present disclosure by those skilled in the art, but do not limit the present disclosure in any way. It should be pointed out that for those of ordinary skill in the art, several adjustments and improvements can be made without departing from the concept of the present disclosure, which are all contemplated in the protection scope of the present disclosure.

Terms used in the present disclosure are defined below.

Antibody refers to an intact monoclonal antibody. The intact antibody consists of two pairs of "light chain" (LC) and "heavy chain" (HC) (the light chain/heavy chain pair is abbreviated as LC/HC). The light and heavy chains of the antibody are polypeptides consisting of several domains. In intact antibodies, each heavy chain includes a heavy chain variable region (abbreviated as HCVR or VH) and a heavy chain constant region. The heavy chain constant region includes heavy chain constant domains CH1, CH2 and CH3 (antibody types IgA, IgD, and IgG) and, optionally, heavy chain constant domain CH4 (antibody types IgE and IgM). Each light chain includes a light chain variable domain VL and a light chain constant domain CL. The structure of a naturally occurring intact antibody, i.e., an IgG antibody, is shown, for example, in FIG. 1. The variable domains VH and VL can be further subdivided into hypervariable regions called complementarity determining regions (CDRs), with more conserved regions called framework regions (FR) distributed between them. VH and VL each consist of three CDRs and four FRs, arranged from the amino terminus to the carboxy terminus in the following order: FR1, CDR1, FR2, CDR2, FR3, CDR3, and FR4 (Janeway, C A, Jr. et al., Immunobiology, 5th Edition, Garland Publishing (2001); and Woof J, Burton D Nat Rev Immunol 4 (2004) 89-99). The two pairs of heavy and light chains (HC/LC) are capable of specifically binding to the same antigen. Thus the intact antibody is a bivalent, monospecific antibody. The "antibody" includes, for example, a mouse antibody, a human antibody, a chimeric antibody, a humanized antibody, and a genetically engineered antibody (variant or mutant antibody), provided that their specific characteristics are retained. Human or humanized antibodies are particularly preferred, especially recombinant human or humanized antibodies. There are five types of heavy chains in mammalian antibodies, which are represented by Greek letters: α, δ, ε, γ, and μ (Janeway, C A, Jr., et al., Immunobiology, 5th Edition, Garland Publishing (2001)). The types of heavy chains present define the types of antibodies. These chains are present in IgA, IgD, IgE, IgG, and IgM antibodies, respectively (Rhoades R A, Pflanzer R G (2002). Human Physiology, 4th Edition, Tom Thomson Learning). Different heavy chains vary in size and composition. Alpha and gamma types contain approximately 450 amino acids, while μ and ε type have approximately 550 amino acids. Each heavy chain has two regions, that is, a constant region and a variable region. The constant regions are identical in all antibodies of the same isotype, but differ in antibodies of different isotypes. The heavy chains γ, α and δ have a constant region consisting of three constant domains CH1, CH2 and CH3 (on a line) and a hinge region for increasing the flexibility (Woof, J., Burton D Nat Rev Immunol 4 (2004) 89-99). The heavy chains μ and ε have a constant region consisting of four constant domains CH1, CH2, CH3 and CH4 (Janeway, C A, Jr., et al., Immunobiology, 5th Edition, Garland Publishing (2001)). The variable regions of the heavy chain vary in antibodies produced by different B cells, but are identical in all antibodies produced by a single type of B cells or B cell clone. The variable region of each heavy chain is approximately 110 amino acids in length and consists of a single antibody domain. In mammals, there are only two types of light chains, called λ and κ. The light chain has two consecutive domains: a constant domain CL and a variable domain VL. The approximate length of the light chain is 211-217 amino acids. Preferably, the light chain is a kappa light chain and the constant domain CL is preferably Cκ.

The Fc portion of an antibody is a term well known to the skilled artisan and is defined based on the cleavage of the antibody with papain. An antibody according to the present disclosure includes, for example, an Fc portion, preferably a human derived Fc portion and preferably all other portions of a human constant region. The Fc portion of the antibody is directly involved in complement activation, C1q binding, C3 activation and Fc receptor binding. Although the effect of an antibody on the complement system depends on specific conditions, binding to C1q is caused by specific binding sites in the Fc portion. Such binding sites are known in the art and are described, for example, in Lukas, T J, et al., J. Immunol. 127 (1981) 2555-2560; Brunhouse, R., and Cebra, J J., Mol. Immunol. 16 (1979) 907-917; Burton, D R, et al., Nature 288 (1980) 338-344; Thommesen, J E, et al., Mol. Immunol.) 37 (2000) 995-1004; Idusogie, E E, et al., J. Immunol. 164 (2000) 4178-4184; Hezareh, M., et al., J. Virol. 75 (2001) 12161-12168; and Morgan, A., et al., Immunology 86 (1995) 319-324; and EP 0 307 434. The binding sites are, for example, L234, L235, D270, N297, E318, K320, K322, P331 and P329 (in accordance with Kabat's EU catalog number). Antibodies of subtypes IgG, IgG2 and IgG3 typically exhibit the capabilities of complement activation, C1q binding and C3 activation, whereas IgG4 does not activate the complement system, does not bind to C1q and does not activate C3.

Humanized antibody refers to an antibody in which the frameworks or "complementarity determining region" (CDRs) have been modified to include CDRs of immunoglobulin that differ in specificity compared to the specificity of the parent immunoglobulin. For example, murine CDRs are grafted into the framework regions of human antibodies to produce "humanized antibodies." (Riechmann, L., et al., Nature 332 (1988) 323-327; and Neuberger, M. S., et al., Nature 314 (1985) 268-270).

Human antibodies include antibodies having variable and constant regions derived from sequences of human immunoglobulin.

Recombinant human antibodies refer to all human antibodies prepared, expressed, produced or isolated by recombination, such as antibodies isolated from host cells, such as NS0 or CHO cells, or antibodies isolated from transgenic animals (eg, mice) with human immunoglobulin genes, or antibodies expressed by a recombinant expression vector transfected into a host cell. The recombinant human antibodies have a variable region and a constant region in a rearranged pattern.

The variable region domain (the light chain (VL) variable region, and the heavy chain (VH) variable region) is each pair of light and heavy chains that are directly involved in the binding of an antibody to an antigen. The human light and heavy chain variable domains have the same general structure and each domain includes four framework regions (FR), which have a sequence that is generally conserved, and are linked through 3 "hypervariable regions" (or Complementarity determining regions, CDRs). The framework regions take a beta-sheet conformation and the CDRs can form a loop that joins the beta-sheet structure. The CDRs in each chain maintain their three-dimensional structure through the framework regions and form an antigen binding site with the CDRs from the other chain.

Bivalent bispecific antibody refers to an antibody as described above, where each of the two pairs of heavy and light chains (HC/LC) specifically binds to a different antigen, i.e., a first heavy chain and a first light chain (derived from an antibody against an antigen A) specifically bind to the antigen A, and a second heavy chain and a second light chain (derived from an antibody against an antigen B) specifically bind to the antigen B. The bivalent bispecific antibody can simultaneously specifically bind to two and no more than two different antigens, in contrast to a monospecific antibody capable of binding only one antigen on the one hand and a tetravalent tetra-specific antibody capable of simultaneously binding to four antigen molecules on the other hand, for example.

Split intein is composed of an N-fragment of intein (In) and a C-fragment of intein (Ic). The gene expressing a precursor protein is split in two open reading frames. The split site is inside the intein sequence. The expression genes of the N-extein (En) and the In of the split intein form a fusion gene, and the fusion protein formed after translation is called an N precursor protein. The expression genes of the Ic of the split intein and the C-extein (Ec) form a fusion gene, and the fusion protein produced after translation is called a C precursor protein. The In or Ic of the split intein alone does not have a protein splicing function. However, after protein translation, the In in the N precursor protein and the Ic in the C precursor protein recognize and bind to each other by a non-covalent bond to form a functional intein, and thus can catalyze the Protein trans-splicing to link two separated exteins (En, EC) with a peptide bond (Ozawa. T., Nat Biotechbol 21 (2003) 287-93).

Protein trans-splicing refers to a protein splicing reaction mediated by a split intein. In this type of splicing process, the In and Ic of the split intein first recognize and bind to each other by a non-covalent bond (FIG. 1). After binding, the structure is properly folded, and the split intein with a re-constructed active center completes the protein splicing reaction following a typical protein splicing route, to link the extein at both sides (Saleh. L., Chemical Record 6 (2006) 183-193).

IN refers to an N-fragment of a split intein alone.

IC refers to a C-fragment of a split intein alone.

Transient transfection is one of the ways to introduce DNA into eukaryotic cells. In transient transfection, a recombinant DNA is introduced into a cell line with high transfection potential to obtain a transient but high level of expression of the gene of interest. The transfected DNA does not have to be integrated into the chromosome of the host, the transfected cells can be harvested in a shorter time than stable transfection, and the expression of the gene of interest in the lysate is detected.

Figure 2:
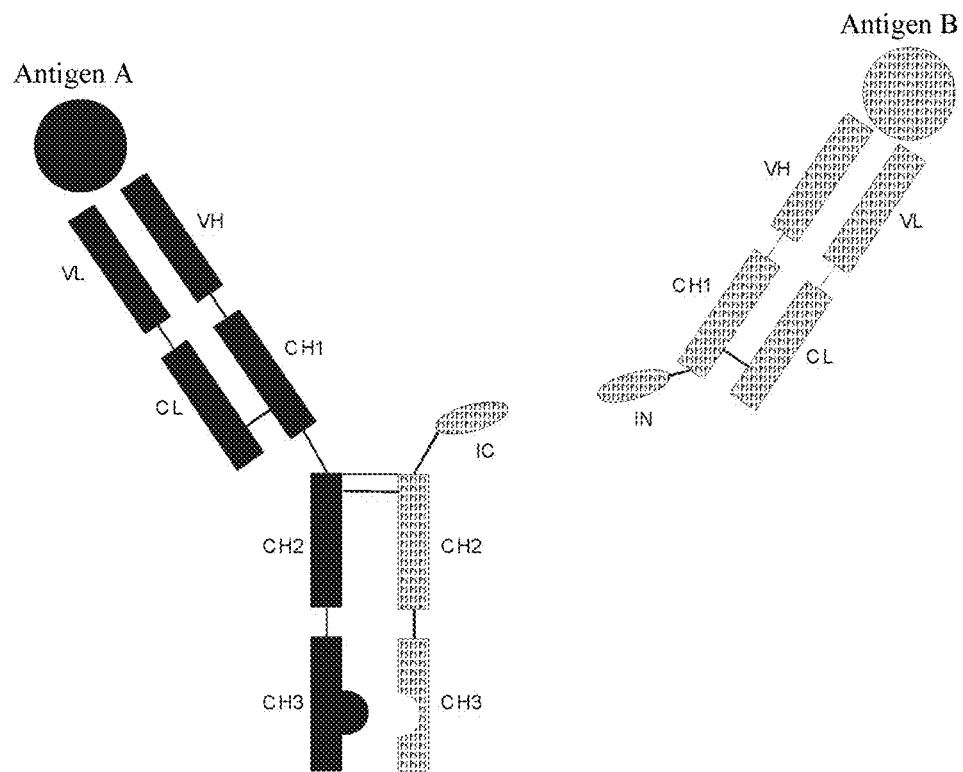
FIG. 2 is a schematic view showing a bispecific antibody split into a portion A antibody comprising a Knob-type heavy chain and a hole-type Fc, and a portion B antibody.
Figure 3:
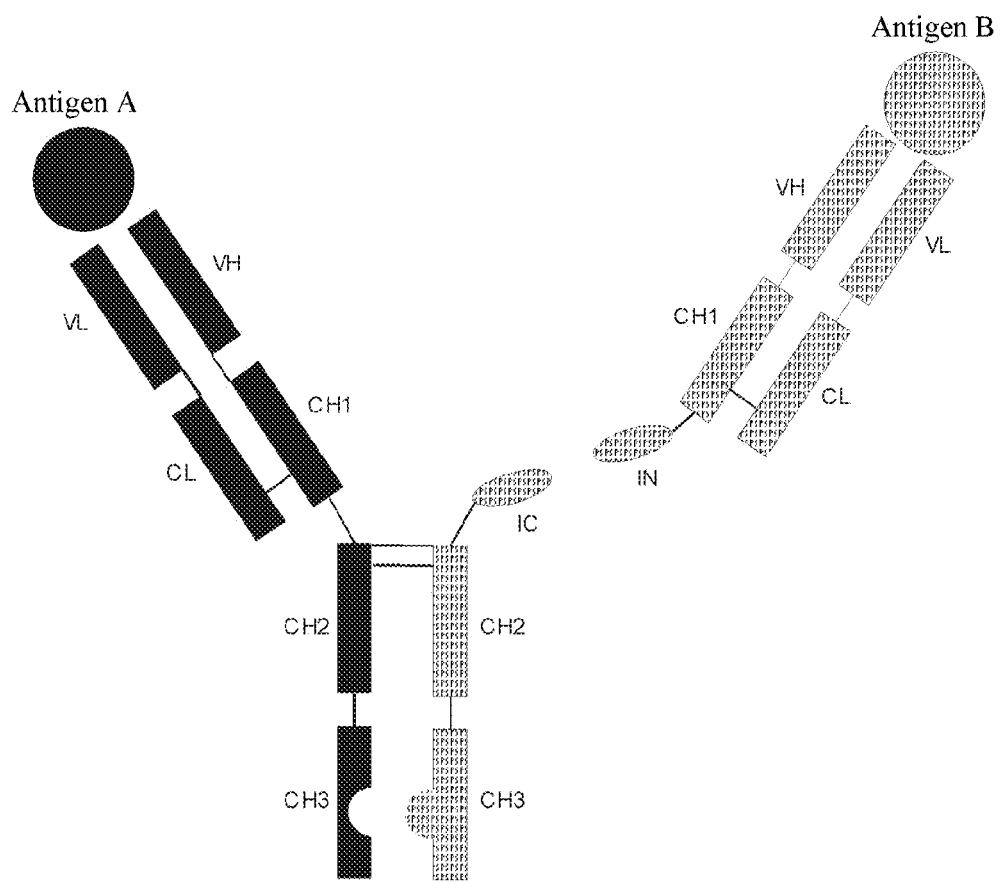
FIG. 3 is a schematic view showing a bispecific antibody split into a portion A antibody comprising a Hole-type heavy chain and a Knob-type Fc, and a portion B antibody.
Figure 4:
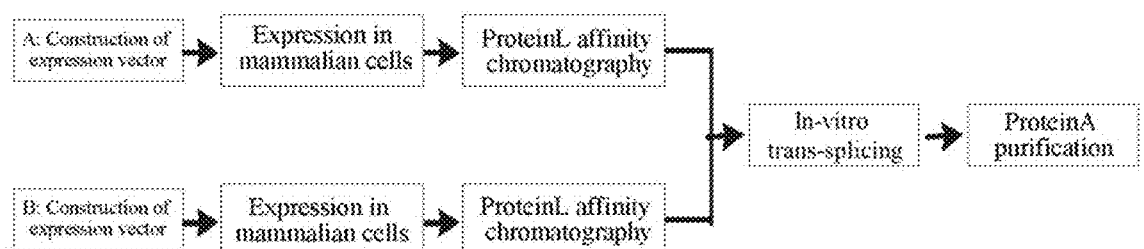
FIG. 4 is a flow chart showing the production of a bispecific antibody.

The present disclosure particularly relates to a method for expressing and preparing bivalent bispecific antibodies. In the present disclosure, a bispecific antibody is split into an antigen A binding portion and an antigen B binding portion for the first time, as shown (in FIGS. 2 and 3), which are expressed separately, and then ligated into a intact antibody by protein trans-splicing by a split intein. The portion A includes a light chain of an antibody A, an intact heavy chain of the antibody A, and an Fc chain having Ic fused to the N terminus. The B includes a light chain of an antibody B and a VH+CH1 chain of the antibody B having In fused to the C terminus In the present disclosure, the trans-splicing function of the split intein is combined with the construction of bispecific antibodies for the first time, and portion A and B antibodies expressed and purified separately are linked to form an intact antibody by means of the trans-splicing function of the split intein. This kind of bispecific antibodies is similar in structure to naturally occurring antibody molecules, thereby avoiding the instability of antibody molecules due to structural differences and the high immunogenicity in vivo. Firstly, an expressed sequence of the obtained antibody is analyzed and split, a mammalian cell expression vector is constructed by whole gene synthesis, and the purified vector is transiently transfected into mammalian cells such as 293E, 293F, and CHO, etc., or stably transfected into mammals cells such as CHO. The fermentation liquors are separately collected and purified by proteinL affinity chromatography. The purified portions A and B are subjected to trans-splicing in vitro, and the spliced product is purified by proteinA affinity chromatography to obtain a relatively pure bispecific antibody. The process flow is shown in FIG. 4.

Figure 5:
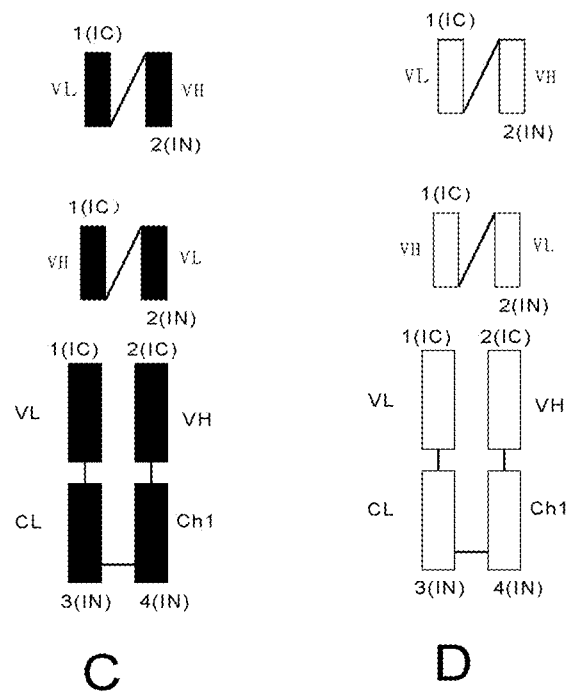
FIG. 5 is a schematic view showing the construction of a fragment-type bispecific antibody.

The method of the present disclosure can also be used to construct a bispecific antibody in which the Fc fragment is defective, for example, only a portion of the CH2 region in the Fc region is retained, or an intact CH2 region and a portion of the CH3 region are retained. In addition, the method is useful in the linkage of any two types of antibody fragments into a novel bispecific antibody. As shown in (FIG. 5), any form of an antibody fragment of a portion C can be trans-spliced with any form of an antibody fragment of a portion D by the split intein.

The method for expressing and preparing a hybrid protein of a novel bivalent bispecific antibody provided in the present disclosure includes specifically the following steps.

1. Construction of Expression Vector

For the construction of expression vectors, general information about the nucleotide sequences of light and heavy chains of human immunoglobulin is provided in Kabat, E A, et al., Sequences of Proteins of Immunological Interest, 5th Edition, Public Health Services, National Institutes of Health, Bethesda, Md. (1991) and in the drugbank database. The amino acids in the antibody chain are numbered and referenced according to the EU numbering (Edelman, G. M., et al., Proc. Natl. Acad. Sci. USA 63(1969) 78-85; Kabat, E. A., et al., Sequences of Proteins of Immunological Interest, 5th Edition, Public Health Service, National Institutes of Health, Bethesda, Md. (1991)). The desired gene segments are prepared by oligonucleotides prepared through chemical synthesis. The 600-1800 bp long gene segment is assembled by annealing and ligation of PCR-amplified oligonucleotides, and then cloned into an expression vector via the indicated restriction sites such as KpnI/BamHI. The DNA sequence of the subcloned gene fragment is verified by DNA sequencing. Infomax's VECTOR NTI ADVANCE suite version 8.0 software is used for sequence construction, mapping, analysis, annotation, and description.

1.1. In order to solve the problem of mispairing of heavy chains, "Knob-into-Hole" is introduced and the VH and CH1 regions of one heavy chain are removed and IC (C-fragment of the split intein) is fused to the N-hinge region of CH2. Thus, the heavy-chain homodimer component formed by the heavy chain that cannot be purified and removed is completely prevented. In order to introduce the "Knob-into-Hole" structure, (threonine) at position 366 in a CH3 region is mutated to W (tryptophan) to form a "Knob" structure. T (threonine) at position 366 in a CH3 region of another heavy chain is mutated to S (serine), L (leucine) at position 368 is mutated to A (alanine), and Y (tyrosine) at position 407 is mutated to V (valine), to form a "Hole" structure. In addition, in order to enhance the binding stability of the CH3 regions, S (serine) at position 354 of the "Knob" chain is mutated to C (cysteine), and Y (tyrosine) at position 349 on the "Hole" chain is mutated to C (cysteine) to enhance the stability between heavy chains by introducing a pair of inter-heavy chain disulfide bonds.

1.2. In order to introduce the split intein, the heavy chain of an antibody B is split into an Fc region and a VH+CH1 region in the heavy chain hinge region of the antibody B, IN (N-fragment of the split intein) is fused to the C-terminus of the CH1 region, and IC (C-fragment of the split intein) is fused to the N terminus of CH2.

Figure 6:
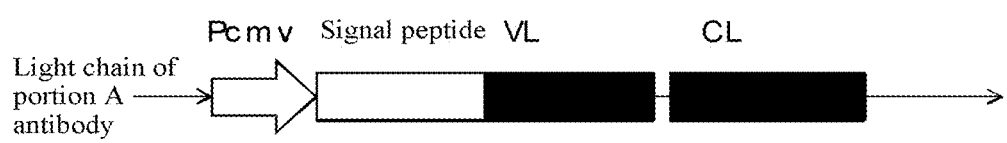
FIG. 6 is a schematic view showing a light chain of a portion A antibody.
Figure 7:
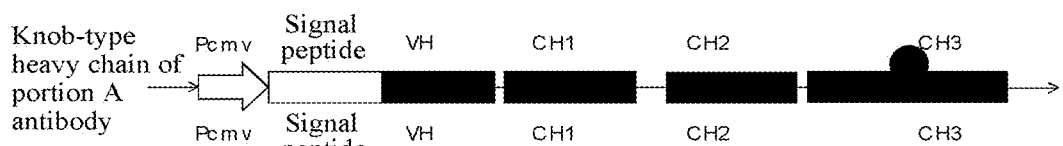
FIG. 7 is a schematic view showing a knob-type heavy chain of the portion A antibody.
Figure 8:
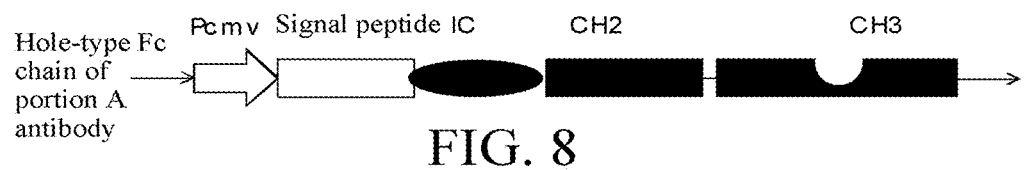
FIG. 8 is a schematic view showing a hole-type Fc chain of the portion A antibody.
Figure 9:
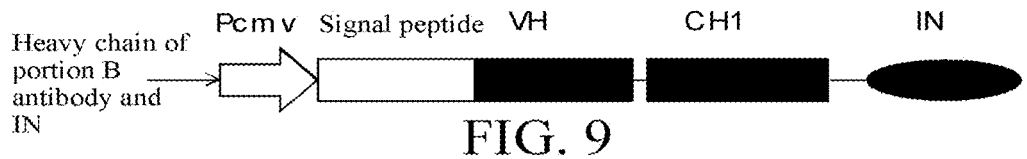
Figure 10:
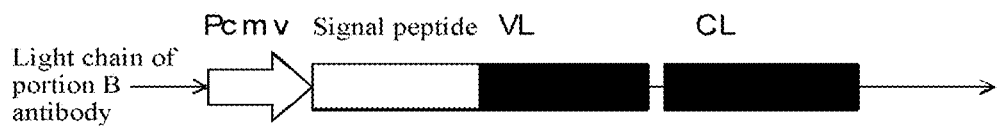
FIG. 10 is a schematic view showing a light chain of the portion B antibody.

1.3.a. As shown (in FIG. 6), the sequence of the light chain of the portion A antibody is a light chain sequence of natural antibody A. As shown (in FIG. 7), in the CH3 region of the heavy chain of the portion A antibody, T (threonine) at position 366 is mutated to W (tryptophan) to form a "Knob" structure; meanwhile S (serine) at position 354 is mutated to C (cysteine). As shown (in FIG. 8), in the CH3 region of the IC+Fc (Fc having C-fragment of the split intein fused to the N terminus) region of the portion A antibody, T (threonine) at position 366 is mutated to S (serine), L (leucine) at position 368 is mutated to A (alanine), and Y (tyrosine) at position 407 is mutated to V (valine) to form a "Hole" structure; meanwhile, Y (tyrosine) at position 349 is mutated to C (cysteine). The heavy chain VH+CH1+IN (the heavy chain variable region of the antibody+CH1 region having N-fragment of the split intein fused to the C terminus) of the portion B antibody is as shown (in FIG. 9). As shown (in FIG. 10), the light chain of the portion B antibody is a light chain sequence of natural antibody B.

Figure 11:
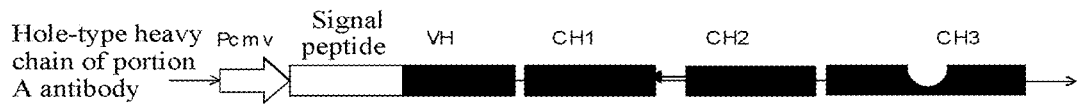
FIG. 11 is a schematic view showing a hole-type heavy chain of a portion A antibody.
Figure 12:
FIG. 12 is a schematic view showing a knob-type Fc chain of the portion A antibody.

1.3.b. As shown (in FIG. 6), the sequence of the light chain of the portion A antibody is a light chain sequence of natural antibody A. As shown (in FIG. 11), in the CH3 region of the heavy chain of the portion A antibody, T (threonine) at position 366 is mutated to S (serine), L (leucine) at position 368 is mutated to A (alanine), and Y (tyrosine) at position 407 is mutated to V (valine), to form a "Hole" structure; meanwhile Y (tyrosine) at position 349 is mutated to C (cysteine). As shown (in FIG. 12), in the CH3 region of the IC+Fc (Fc having C-fragment of the split intein fused to the N terminus) region of the portion A antibody, T (threonine) at position 366 is mutated to W (tryptophan) to form a "Knob" structure; meanwhile, S (serine) at position 354 is mutated to C (cysteine). The heavy chain VH+CH1+IN (the heavy chain variable region of the antibody+CH1 region having N-fragment of the split intein fused to the C terminus) of the portion B antibody is as shown (in FIG. 9). As shown (in FIG. 10), the light chain of the portion B antibody is a light chain sequence of natural antibody B.

1.3.c. Construction of expression vectors of small fragment antibodies As shown (in FIG. 5), any one of the antibody fragments is selected from the group C, and N-fragment of the split intein is fused at the position IN shown in FIG. 5. Also, any one of the antibody fragments is selected from the group D, and C-fragment of the split intein is fused at the position IC shown in FIG. 5

Figure 13:
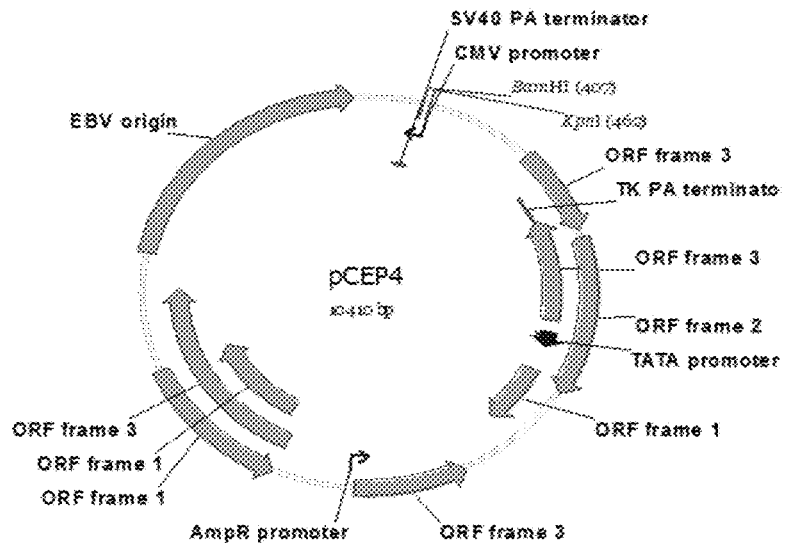
FIG. 13 is a map of pCEP4 expression vector.

1.4. The gene sequences designed in the above 1.3 are subjected to whole-gene synthesis. Restriction endonuclease cleavage sites such as KpnI/BamHI are added at the two sides of the start codon and the stop codon by polymerase chain reaction (PCR). The genes are respectively inserted into a mammalian cell expression vector containing CMV promoter, the subclones are sequenced, and the plasmids are extracted. For transient transfection, a larger amount of plasmid is prepared with a plasmid preparation (omega) from transformed $E.\ coli$ culture. In addition to the antibody expressing region, the vector includes an origin of replication which allows the plasmid to replicate in $E.\ coli$ and the P3-lactamase gene, which confers ampicillin resistance in $E.\ coli$. The transcription unit of an antibody gene consists of a unique restriction site at the 5' end, an immediate early enhancer and promoter from human cytomegalovirus, followed by an intron A sequence, a 5' untranslated region of a human antibody gene, a signal peptide sequence of an immunoglobulin light chain (or other signal peptide sequence), a 3' untranslated region with an signal sequence A, and a unique restriction site at the 3' end, in the case of cDNA construction (FIG. 13).

2. For example, standard cell culture techniques described in Current Protocols in Cell Biology (2000), Bonifacino, J S, Dasso, M., Harford, J B, Lippincott-Schwartz, J. and Yamada, K M (ed.), John Wiley & Sons, Inc can be used. The portions A and B antibodies are expressed by transiently co-transfecting HEK293-E cells grown in suspension or HEK29-F cells grown in suspension with various expression vectors, as described below.

2.1. Transient transfection of HEK293-E system. The portions A and B of a bispecific antibody are produced by co-transfecting HEK293-E cells (human embryonic kidney cell line 293 expressing Epstein-Barr virus nuclear antigen; American Type Culture Center, accession number ATCC #CRL-10852, Lot. 959 218) respectively with three expression vectors and two expression vectors. The cells are cultured in SFX4HEK293 medium (HYCLONE) and GIBCO FREESTYLE 293 medium in a ratio of 1:1 to which 100 µg/ml GENETICIN aminoglycoside antibiotic is added, and the cells are diluted to $1.5\text{-}2.5 \times 10^6$ cells/ml with fresh medium one day before transfection and incubated at 37° C. and 120 rpm in 5% $CO_2$ for transfection on the following day. Taking a 1 L shaking flask (CORNING) as an example, the cells are collected by centrifugation at 500-2000 rpm for 5-10 min on the following day, and then washed several times with (10-50 ml) GIBCO FREESTYLE 293 medium. The cells are collected by centrifugation at 500-2000 rpm for 5-10 min, and then resuspended in 150 ml GIBCO FREESTYLE 293 medium to a cell density of $2\text{-}6 \times 10^6$ cells/ml in a new 1 L shaking flask (CORNING). Plasmids for co-transfection are used in an amount of 0.25-1.5 µg DNA per $10^6$ cells at equimolar ratio of the vectors of genes encoding various chains, and the DNAs are diluted with GIBCO FREESTYLE 293 medium to (40 ng/µL). DNA: PEI (polyscience cationic transfection reagent)=1:2-1:6 are added to the uniformly mixed DNAs and incubated for 5-20 min at room temperature. The cell suspension is added, mixed, and transfected for 4 hours at 37° C. and 120 rpm, in 5% $CO_2$. Equal volume of pre-warmed SFX4HEK293 medium is added after 4 hours, and then 100 µg/ml GENETICIN aminoglycoside antibiotic is added and incubated at 37° C. and 120 rpm, in 5% $CO_2$ for 5-10 days. The supernatant is directly collected for purification or the supernatant is collected and stored at −80° C.

2.1.a. PEI-mediated co-transfection of HEK293-E cells with three expression vectors of portion A antibody SFX4HEK293 medium (HYCLONE) and GIBCO FREESTYLE 293 medium are added in a ratio of 1:1, 100 µg/ml GENETICIN aminoglycoside antibiotic is added, and the cells are diluted to 1.5-2.5×$10^6$ cells/nil with fresh medium one day before transfection and incubated at 37° C. and 120 rpm in 5% $CO_2$ for transfection on the following day. Taking a 1 L shaking flask (CORNING) as an example, the cells are collected by centrifugation at 500-2000 rpm for 5-10 min on the following day, and then washed several times with (10-50 ml) GIBCO FREESTYLE 293 medium. The cells are collected by centrifugation at 500-2000 rpm for 5-10 min, and then resuspended in 150 ml GIBCO FREESTYLE 293 medium to a cell density of 2-6×$10^6$ cells/ml in a new 1 L shaking flask (CORNING). The three expression vectors containing genes encoding the portion A antibody are mixed uniformly at an equimolar ratio in an amount of 0.25-1.5 µg DNA per $10^6$ cells, and the DNAs are diluted with GIBCO FREESTYLE 293 medium to (40 ng/µL). DNA: PEI (polyscience cationic transfection reagent)=1:2-1:6 are added to the uniformly mixed DNAs and incubated for 5-20 min at room temperature. The cell suspension is added, mixed, and transfected for 4 hours at 37° C. and 120 rpm, in 5% $CO_2$. Equal volume of pre-warmed SFX4HEK293 medium is added after 4 hours, and then 100 µg/ml GENETICIN aminoglycoside antibiotic is added and incubated at 37° C. and 120 rpm, in 5% $CO_2$ for 5-10 days, to obtain the portion A antibody. The supernatant is directly collected for purification or the supernatant is collected and stored at −80° C.

2.1.b. PEI-mediated co-transfection of HEK293-E cells with two expression vectors of portion B antibody SFX4HEK293 medium (HYCLONE) and GIBCO FREESTYLE 293 medium are added in a ratio of 1:1, 100 µg/ml GENETICIN aminoglycoside antibiotic is added, and the cells are diluted to 1.5-2.5×$10^6$ cells/ml with fresh medium one day before transfection and cultured at 37° C. and 120 rpm in 5% $CO_2$ for transfection on the following day. Taking a 1 L shaking flask (CORNING) as an example, the cells are collected by centrifugation at 1000 rpm for 5 min on the following day, and then washed several times with 50 ml GIBCO FREESTYLE 293 medium. The cells are collected by centrifugation at 1000 rpm for 5 min, and then resuspended in 150 ml GIBCO FREESTYLE 293 medium to a cell density of 2-6×$10^6$ cells/nil in a new 1 L shaking flask (CORNING). The two expression vectors containing genes encoding the portion A antibody are mixed uniformly at an equimolar ratio in an amount of 0.25-1.5 µg DNA per $10^6$ cells, and the DNAs are diluted with GIBCO FREESTYLE 293 medium to (40 ng/µL). DNA: PEI (polyscience cationic transfection reagent)=1:2-1:6 are added to the uniformly mixed DNAs and incubated for 5-20 min at room temperature. The cell suspension is added, mixed, and transfected for 4 hours at 37° C. and 120 rpm, in 5% $CO_2$. Equal volume of pre-warmed SFX4HEK293 medium is added after 4 hours, and then 100 µg/ml GENETICIN aminoglycoside antibiotic is added and incubated at 37° C. and 120 rpm, in 5% $CO_2$ for 5-10 days, to obtain the portion B antibody. The supernatant is directly collected for purification or the supernatant is collected and stored at −80° C.

3. Protein L affinity purification of antibody in fermentation liquor. The protein is purified from the filtered cell culture supernatant following a standard procedure. Briefly, the antibody is subjected to protein L affinity chromatography (GE HEALTHCARE) and washed with PBS (containing 20 mM phosphate, 150 mM NaCl pH 6.8-7.4). The impurity components are washed off with 100 mM citrate buffer at pH 5.0, and the antibody is eluted with 100 mM citrate buffer at pH 3.0, and then immediately neutralized with 1 M tris-Hcl buffer at pH 9.0. A portion of the sample is provided for subsequent protein analysis by for example, SDS-PAGE. The monomeric antibody components are pooled for subsequent in-vitro ram splicing mediated by the intein. If necessary, the monomeric antibody components are concentrated using the MILLIPORE AMICON ULTRA (30 MWCO) ultrafiltration centrifuge tube, frozen and stored at −20° C. or −80° C.

Figure 14:
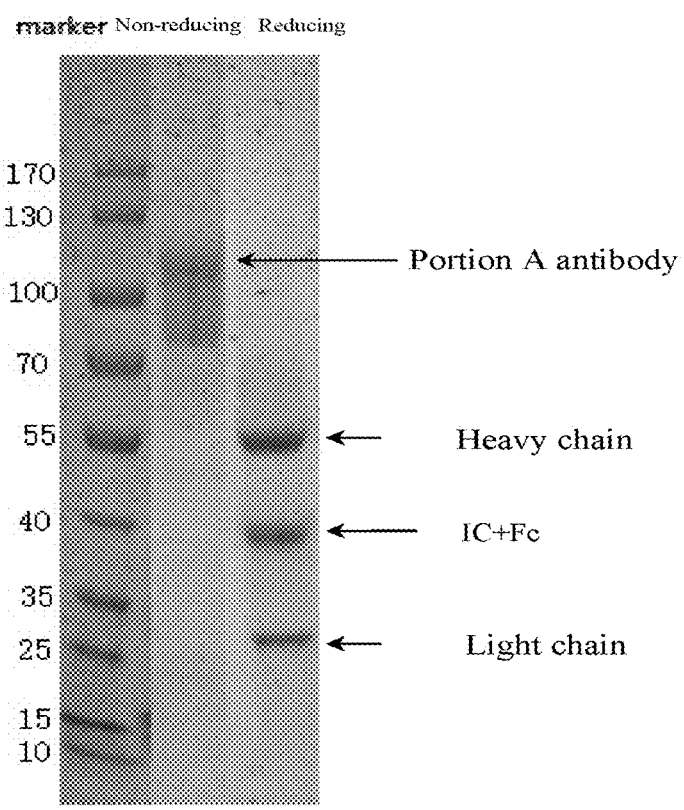
FIG. 14 is a SDS-PAGE electrophoretogram of a purified product co-transfected with three expression vectors of a portion A antibody of a bispecific antibody.

3.1. Protein L affinity purification of portion A antibody in fermentation liquor co-transfected with triple expression vectors The protein is purified from the filtered cell culture supernatant following a standard procedure. The supernatant from which the cells are filtered off is mixed with PBS (containing 20 mM phosphate, and 150 mM NaCl pH 6.8-7.4), run through a Protein L affinity chromatographic column pre-equilibrated with PBS, and washed with PBS after loading. The impurity components are washed off with 100 mM citrate buffer at pH 5.0, and the antibody is eluted with 100 mM citrate buffer at pH 3.0, and then immediately neutralized with 1 M tris-Hcl buffer at pH 9.0. A portion of the sample is provided for subsequent protein analysis by, for example, SDS-PAGE. As shown in (FIG. 14), in the non-reduced sample, assembled portion A antibody of the bispecific antibody appears at around 103 KD. In the reduced sample, the heavy chain of 55 KD, the IC +Fc chain of 40 KD, and the light chain of 25 KD appear. The monomeric antibody components are pooled for subsequent in-vitro trans splicing mediated by the intein. If necessary, the monomeric antibody components are concentrated using the MILLIPORE AMICON ULTRA (30 MWCO) ultrafiltration centrifuge tube, frozen and stored at −20° C. or −80° C.

Figure 15:
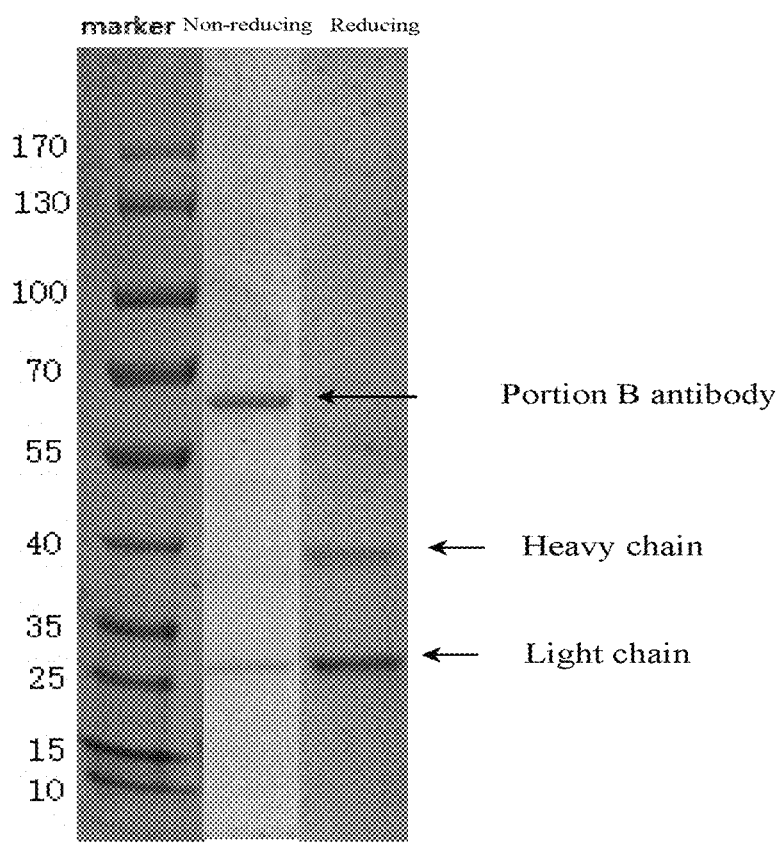
FIG. 15 is a SDS-PAGE electrophoretogram of a purified product co-transfected with a two expression vector of a portion B antibody of a bispecific antibody.

3.2. Protein L affinity purification of portion B antibody in fermentation liquor co-transfected with two expression vectors The protein is purified from the filtered cell culture supernatant following a standard procedure. The supernatant from which the cells are filtered off is mixed with PBS (containing 20 mM phosphate, and 150 mM NaCl pH 6.8-7.4), run through a Protein L affinity chromatographic column pre-equilibrated with PBS, and washed with PBS after loading. The impurity components are washed off with 100 mM citrate buffer at pH 5.0, and the antibody is eluted with 100 mM citrate buffer at pH 3.0, and then immediately neutralized with 1 M tris-Hcl buffer at pH 9.0. A portion of the sample is provided for subsequent protein analysis by, for example, SDS-PAGE. As shown in (FIG. 15), in the non-reduced sample, assembled portion B antibody of the bispecific antibody appears at around 60 KD. In the reduced sample, the VH+CH1+IN of 35 KD and the light chain of 25 KD appear. The monomeric antibody components are pooled for subsequent in-vitro trans splicing mediated by the intein. If necessary, the monomeric antibody components are concentrated using the MILLIPORE AMICON ULTRA (30 MWCO) ultrafiltration centrifuge tube, frozen and stored at −20° C. or −80° C.

Figure 16:
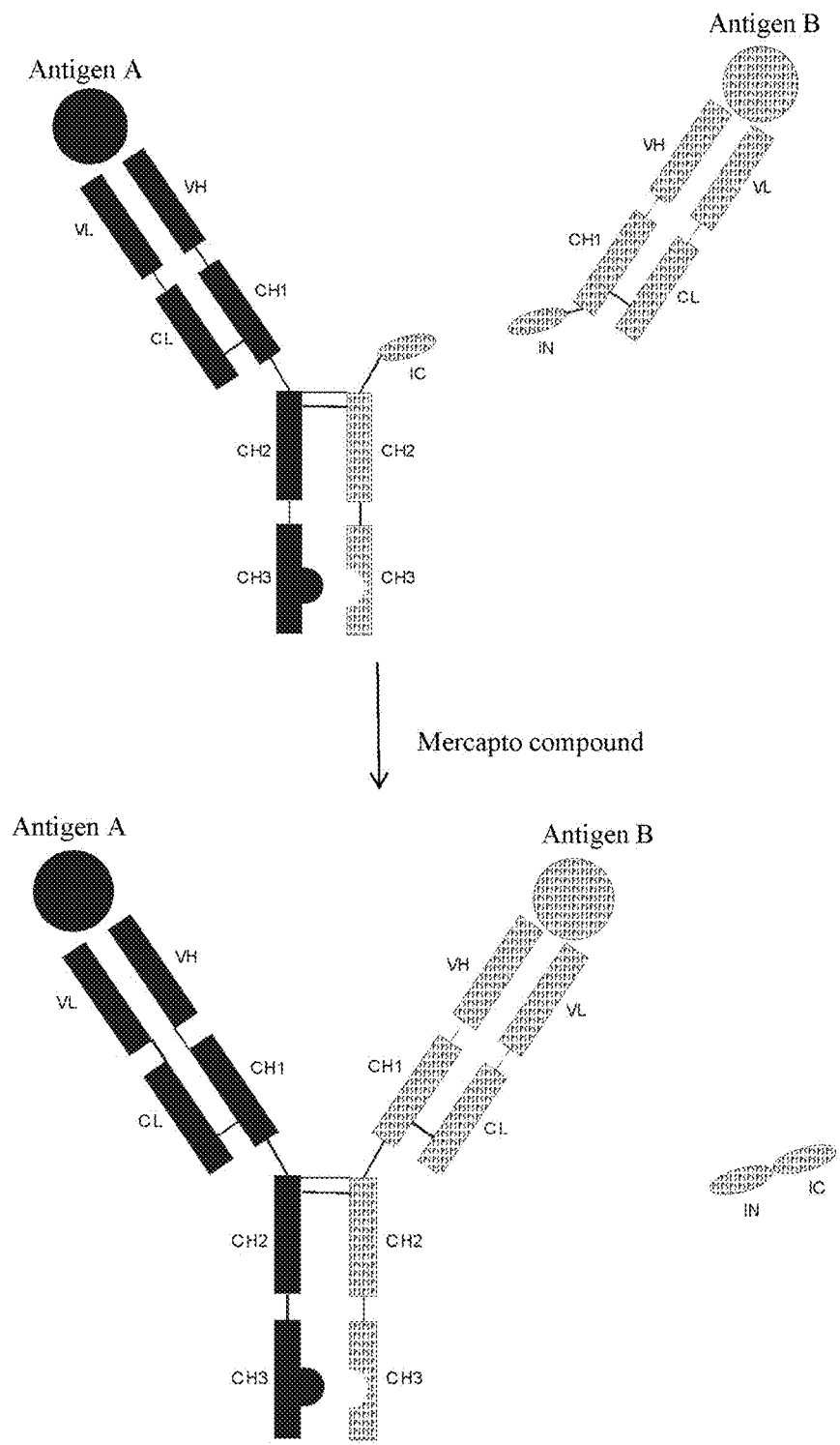
FIG. 16 is a schematic view showing the splicing (type I) of a portion A antibody and a portion B antibody mediated by a split intein.
Figure 17:
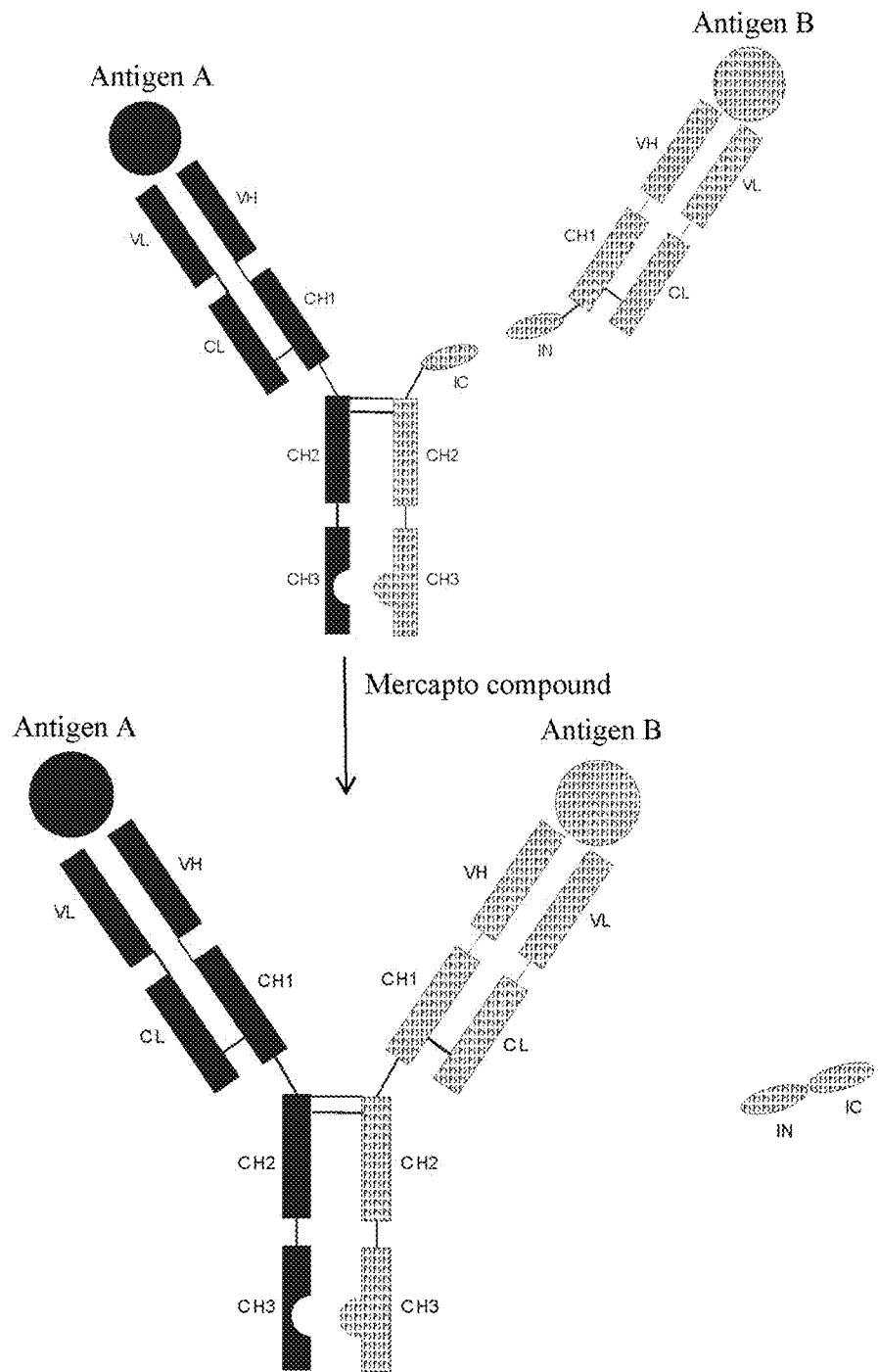
FIG. 17 is a schematic view showing the splicing (type II) of a portion A antibody and a portion B antibody mediated by a split intein.
Figure 18:
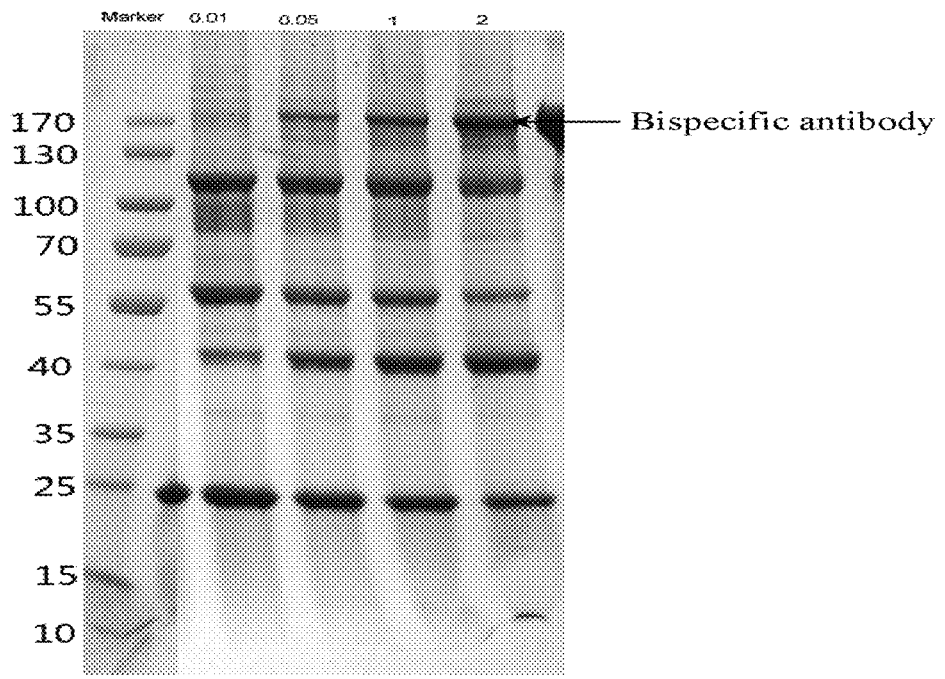
FIG. 18 is a schematic view showing the trans-splicing into a bispecific antibody induced by a split intein at various DTI concentrations (mM)
Figure 19:
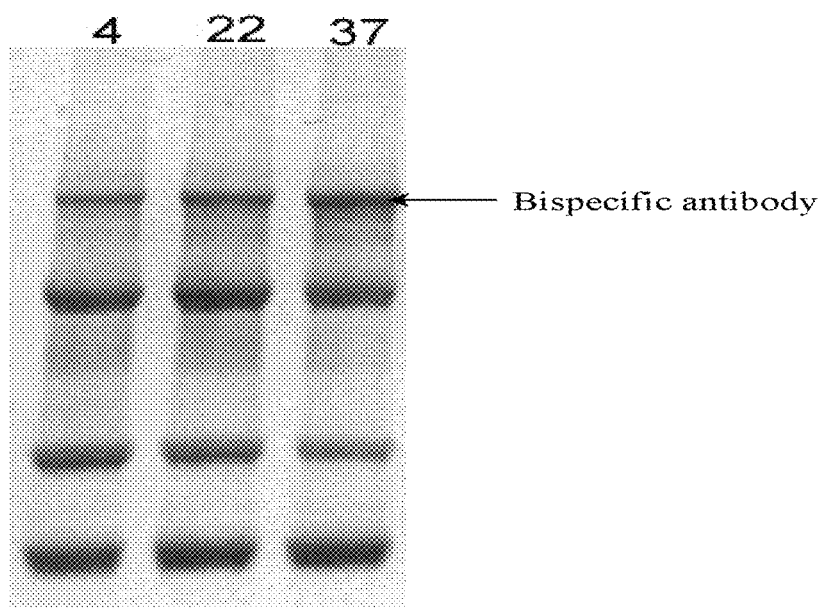
FIG. 19 is a schematic view showing the ram-splicing into a bispecific antibody induced by a split intein at various temperatures (° C.)
Figure 20:
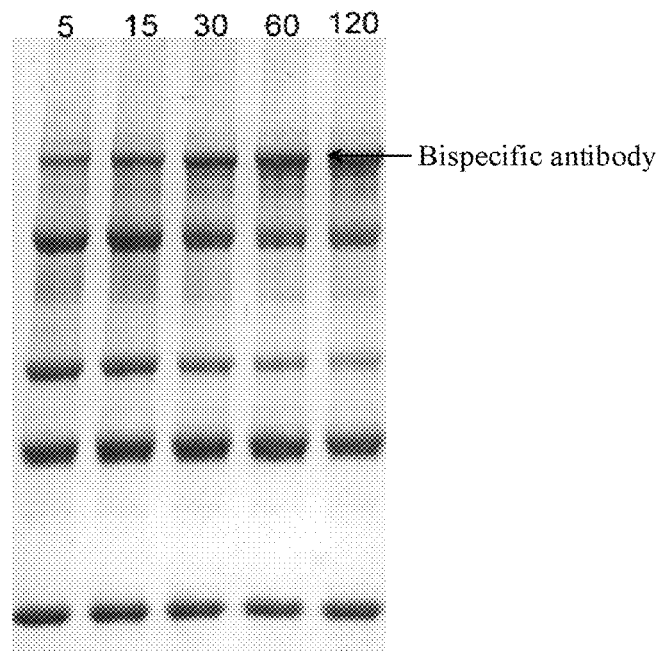
FIG. 20 is a schematic view showing the trans-splicing into a bispecific antibody induced by a split intein at various reaction times (min)

4.1. The in vitro trans-splicing mediated by the split intein of the portions A and B is as shown in (in FIGS. 16 and 17). The portion A and B antibodies purified in Step 3 are mixed at a molar ratio of 1:1, and 0.05 mM to 2 mM DTT or (3-mercaptoethanol is added. As shown in (FIG. 18), the final concentration of DTT is 0.01 mM, 0.05 mM, 1 mM, 2 mM respectively. The results show that DTT can induce the occurrence of split intein-mediated trans-splicing at a concentration of 0.05 mM, and an obvious band of the bispecific antibody appears at 150 KD. Trans-splicing reaction mediated by the split intein is induced to occur by a sulfhydryl compound such as TCEP. 1 mM DTT or TCEP is added to the splicing reaction system at 4-37° C., and incubate respectively at 4, 22, and 37° C. As shown (in FIG. 19), the reaction occurs at 4° C., the reaction efficiency is higher at 22 and 37° C., and an obvious band of the bispecific antibody appears at 150 KD. 1 mM DTT is added to the splicing reaction system, and incubate at 37° C. for 5 min, 15 min, 30 min, 60 min, and 120 min, respectively. As shown in (FIG. 20), a bispecific antibody is produced at 5 min, and the reaction reaches a plateau at 60 min. At the end of the reaction, the sulfhydryl compound needed to be removed, and the sulfhydryl compound could be removed by adding an oxidizing agent such as hydrogen peroxide, or removed by dialysis. Further, the sulfhydryl compound might be diluted to below a working concentration by high-fold dilution with a buffer to achieve the purpose of terminating the reaction. The reaction is terminated and a sample is taken for detection by non-reducing SDS-PAGE.

4.2. The in-vitro trans-splicing mediated by the split intein of the portions C and D is as described in 4.1.

5.1. Protein A purification of product obtained after trans-splicing mediated by split intein of portions A and B The protein is purified front the reaction mixture of Step 4 following a standard procedure. The sample is mixed with PBS (containing 20 mM phosphate, and 150 mM NaCl pH 6.8-7.4), run through a ProteinA affinity chromatographic column pre-equilibrated with PBS, and washed with PBS after loading. The impurity components are washed off with 100 mM citrate buffer at pH 5.0, and the antibody is eluted with 100 mM citrate buffer at pH 3.0, and then immediately neutralized with 1 M tris-Hcl buffer at pH 9.0. A portion of the sample is provided for subsequent protein analysis by, for example, SDS-PAGE. As shown in (FIG. 21), in the non-reduced sample, an obvious hand of a bispecific antibody formed by trans-splicing mediated by the split intein appears at 150 KD and the purity is high. In the reduced sample, only a heavy chain of about 50 KD and a light chain of about 25 KD appear. The monomeric antibody component is pooled. If necessary, the monomeric antibody component is concentrated using the MILLIPORE AMICON ULTRA (30 MWCO) ultrafiltration centrifuge tube, frozen and stored at −20° C. or −80° C.; or purified by, for example, ion exchange chromatography, hydrophobic chromatography, and molecular exclusion chromatography, to achieve a higher purity.

5.2. Purification of product formed by trans-splicing of portions C and D mediated by split intein For the product obtained by trans-splicing of the portions C and D, purification by recombinant protein purification methods such as ion exchange chromatography, hydrophobic chromatography and size exclusion chromatography is required.

Specific applications are shown in the following examples.

Example 1: Construction of CD3×Her2 Bispecific Antibody 1.1. Construction of Expression Vectors For the construction of expression vectors, general information about the nucleotide sequences of light and heavy chains of human immunoglobulin is provided in Kabat, E A, et al., Sequences of Proteins of Immunological Interest, 5th Edition, Public Health Services, National Institutes of Health, Bethesda, Md. (1991) and in the drugbank database. The amino acids in the antibody chain are numbered and referenced according to the EU numbering (Edelman, G. M., et al., Proc. Natl. Acad. Sci. USA 63(1969) 78-85; Kabat, E. A., et al., Sequences of Proteins of Immunological Interest, 5th Edition, Public Health Service, National Institutes of Health, Bethesda, Md. (1991)). The CD3 antibody sequence was derived from humanized OKT3 antibody sequence and the desired gene segments were prepared by oligonucleotides prepared through chemical synthesis. The 600-1800 bp long gene segment was assembled by annealing and ligation of PCR-amplified oligonucleotides, and then cloned into an expression vector via the indicated restriction sites such as KpnI/BamHI. The DNA sequence of the subcloned gene fragment was verified by DNA sequencing. Infomax's VECTOR NTI ADVANCE suite version 8.0 software was used for sequence construction, mapping, analysis, annotation, and description. In order to solve the problem of mispairing of heavy chains, "Knob-into-Hole" was introduced, the VH and CH1 regions of one heavy chain are removed, and IC (C-fragment of the split intein) was fused to the N-hinge region of CH2. Thus, the heavy-chain homodimer component formed by the heavy chain that cannot be purified and removed was completely prevented. In order to introduce the "Knob-into-Hole" structure, (threonine) at position 366 in a CH3 region of the CD3 antibody was mutated to W (tryptophan) to form a "Knob" structure. T (threonine) at position 366 in a CH3 region of the Her2 antibody was mutated to S (serine), L (leucine) at position 368 was mutated to A (alanine), and Y (tyrosine) at position 407 was mutated to V (valine), to form a "Hole" structure. In addition, in order to enhance the binding stability of the CH3 regions, S (serine) at position 354 of the "Knob" chain was mutated to C (cysteine), and Y (tyrosine) at position 349 on the "Hole" chain was mutated to C (cysteine) to enhance the stability between heavy chains by introducing a pair of inter-heavy chain disulfide bonds.

1.1.a. The CD3 antibody was used as the portion A antibody, and the expression vector of each chain was respectively designed on the basis of the following. A light chain of the portion A antibody was designed as shown (in FIG. 6), a knob heavy chain of the portion A antibody was designed as shown (in FIG. 7), and a hole Fc chain of the portion A antibody was designed as shown (in FIG. 8). The Her2 antibody was used as the portion B antibody, and the expression vector of each chain was respectively designed on the basis of the following. A heavy chain IN of the portion B antibody was designed as shown (in FIG. 9) and a light chain of the portion B antibody was designed as shown (in FIG. 10).

1.1.b. The CD3 antibody was used as the portion A antibody, and the expression vector of each chain was respectively designed on the basis of the following. A light chain of the portion A antibody was designed as shown (in FIG. 6), a hole heavy chain of the portion A antibody was designed as shown (in FIG. 11), and a knob Fc chain of the portion A antibody was designed as shown (in FIG. 12). The Her2 antibody was used as the portion B antibody, and the expression vector of each chain was respectively designed on the basis of the following. A heavy chain IN of the portion B antibody was designed as shown (in FIG. 9) and a light chain of the portion B antibody was designed as shown (in FIG. 10).

1.1.c. The Her2 antibody was used as the portion A antibody, and the expression vector of each chain was respectively designed on the basis of the following. A light chain of the portion A antibody was designed as shown (in FIG. 6), a knob heavy chain of the portion A antibody was designed as shown (in FIG. 7), and a hole Fc chain of the portion A antibody was designed as shown (in FIG. 8). The CD3 antibody was used as the portion B antibody, and the expression vector of each chain was respectively designed on the basis of the following. A heavy chain IN of the portion B antibody was designed as shown (in FIG. 9) and a light chain of the portion B antibody was designed as shown (in FIG. 10).

1.1.d. The Her2 antibody was used as the portion A antibody, and the expression vector of each chain was respectively designed on the basis of the following. A light chain of the portion A antibody was designed as shown (in FIG. 6), a hole heavy chain of the portion A antibody was designed as shown (in FIG. 11), and a knob Fc chain of the portion A antibody was designed as shown (in FIG. 12). The CD3 antibody was used as the portion B antibody, and the expression vector of each chain was respectively designed on the basis of the following. A heavy chain IN of the portion B antibody was designed as shown (in FIG. 9) and a light chain of the portion B antibody was designed as shown (in FIG. 10).

1.2. Expression of Transiently Transfected HEK-293E Cells

Transient transfection of HEK293-E system The portions A and B of a bispecific antibody were produced by co-transfecting HEK293-E cells (human embryonic kidney cell line 293 expressing Epstein-Barr virus nuclear antigen; American Type Culture Center, accession number ATCC #CRL-10852, Lot. 959 218) respectively with three expression vectors and two expression vectors. The cells were cultured in SFX4HEK293 medium (HYCLONE) and GIBCO FREESTYLE 293 medium in a ratio of 1:1 to which 100 μg/ml GENETICIN aminoglycoside antibiotic was added, and the cells were diluted to 1.5-2.5×10$^6$ cells/ml with fresh medium one day before transfection and incubated at 37° C. and 120 rpm in 5% $CO_2$ for transfection on the following day. Taking a 1 L shaking flask (CORNING) as an example, the cells were collected by centrifugation at 1000 rpm for 5 min on the following day, and then washed once with 50 ml GIBCO FREESTYLE 293 medium. The cells were collected by centrifugation at 1000 rpm for 5 min, and then resuspended in 150 ml GIBCO FREESTYLE 293 medium to a cell density of 4×10$^6$ cells/ml in a new 1 L shaking flask (CORNING). Plasmids for co-transfection were used in an amount of 0.5 μg DNA per 10$^6$ cells at equimolar ratio of the vectors of genes encoding various chains, and the DNAs were diluted with GIBCO FREESTYLE 293 medium to (40 ng/μL). DNA: PEI (polyscience cationic transfection reagent)=1:3 were added to the uniformly mixed DNAs and incubated for 20 min at room temperature. The cell suspension was added, mixed, and transfected for 4 hours at 37° C. and 110 rpm, in 5% $CO_2$. Equal volume of pre-warmed SFX4HEK293 medium was added after 4 hours, and then 100 μg/ml GENETICIN aminoglycoside antibiotic was added and incubated at 37° C. and 130 rpm, in 5% $CO_2$ for 10 days. The supernatant was directly collected for purification or the supernatant was collected and stored at −80° C.

1.2.a. PEI-mediated co-transfection of HEK293-E cells with three expression vectors of portion A antibody constructed in 1.1.a. The cells were incubated in SFX4HEK293 medium (HYCLONE) and GIBCO FREESTYLE 293 medium in a ratio of 1:1 to which 100 μg/ml GENETICIN aminoglycoside antibiotic was added, and the cells were diluted to 1.5-2.5×10$^6$ cells/ml with fresh medium one day before transfection and incubated at 37° C. and 120 rpm in 5% $CO_2$ for transfection on the following day. Taking a 1 L shaking flask (CORNING) as an example, the cells were collected by centrifugation at 1000 rpm for 5 min on the following day, and then washed once with 50 ml GIBCO FREESTYLE 293 medium. The cells were collected by centrifugation at 1000 rpm for 5 min, and then resuspended in 150 ml GIBCO FREESTYLE 293 medium to a cell density of 4×10$^6$ cells/ml in a new 1 L shaking flask (CORNING). Plasmids for co-transfection were used in an amount of 0.5 μg DNA per 10$^6$ cells at equimolar ratio of the vectors of genes encoding various chains, and the DNAs were diluted with GIBCO FREESTYLE 293 medium to (40 ng/μL). DNA: PEI (polyscience cationic transfection reagent)=1:3 were added to the uniformly mixed DNAs and incubated for 20 min at room temperature. The cell suspension was added, mixed, and transfected for 4 hours at 37° C. and 110 rpm, in 5% $CO_2$. Equal volume of pre-warmed SFX4HEK293 medium was added after 4 hours, and then 100 μg/ml GENETICIN aminoglycoside antibiotic was added and incubated at 37° C. and 130 rpm, in 5% $CO_2$ for 10 days. The supernatant was directly collected for purification or the supernatant was collected and stored at −80° C.

1.2.b. PEI-mediated co-transfection of HEK293-E cells with three expression vectors of portion A antibody constructed in 1.1.b. The cells were cultured in SFX4HEK293 medium (HYCLONE) and GIBCO FREESTYLE 293 medium in a ratio of 1:1 to which 100 μg/ml GENETICIN aminoglycoside antibiotic was added, and the cells were diluted to 1.5-2.5×10$^6$ cells/nil with fresh medium one day before transfection and incubated at 37° C. and 120 rpm in 5% $CO_2$ for transfection on the following day. Taking a 1 L shaking flask (CORNING) as an example, the cells were collected by centrifugation at 1000 rpm for 5 min on the following day, and then washed once with 50 ml GIBCO FREESTYLE 293 medium. The cells were collected by centrifugation at 1000 rpm for 5 min, and then resuspended in 150 ml GIBCO FREESTYLE 293 medium to a cell density of 4×10$^6$ cells/ml in a new 1 L shaking flask (CORNING). Plasmids for co-transfection were used in an amount of 0.5 μg DNA per 10$^6$ cells at equimolar ratio of the vectors of genes encoding various chains, and the DNAs were diluted with GIBCO FREESTYLE 293 medium to (40 ng/μL). DNA: PEI (polyscience cationic transfection reagent)=1:3 were added to the uniformly mixed DNAs and incubated for 20 min at room temperature. The cell suspension was added, mixed, and transfected for 4 hours at 37° C. and 110 rpm, in 5% $CO_2$. Equal volume of pre-warmed SFX4HEK293 medium was added after 4 hours, and then 100 μg/ml GENETICIN aminoglycoside antibiotic was added and incubated at 37° C. and 130 rpm, in 5% $CO_2$ for 10 days. The supernatant was directly collected for purification or the supernatant was collected and stored at −80° C.

1.2.c. PEI-mediated co-transfection of HEK293-E cells with two expression vectors of portion A antibody (Her2) constructed in 1.1.c. The cells were cultured in SFX4HEK293 medium (HYCLONE) and GIBCO FREESTYLE 293 medium (Gibco) in a ratio of 1:1 to which 100 μg/ml GENETICIN aminoglycoside antibiotic was added, and the cells were diluted to 1.5-2.5×10$^6$ cells/ml with fresh medium one day before transfection and incubated at 37° C. and 120 rpm in 5% $CO_2$ for transfection on the following day. Taking a 1 L shaking flask (CORNING) as an example, the cells were collected by centrifugation at 1000 rpm for 5 min on the following day, and then washed once with 50 ml GIBCO FREESTYLE 293 medium. The cells were collected by centrifugation at 1000 rpm for 5 min, and then resuspended in 150 ml GIBCO FREESTYLE 293 medium to a cell density of $4\times10^6$ cells/ml in a new 1 L shaking flask (CORNING). Plasmids for co-transfection were used in an amount of 0.5 μg DNA per $10^6$ cells at equimolar ratio of the vectors of genes encoding various chains, and the DNAs were diluted with GIBCO FREESTYLE 293 medium to (40 ng/μL). DNA: PEI (polyscience cationic transfection reagent)=1:3 were added to the uniformly mixed DNAs and incubated for 20 min at room temperature. The cell suspension was added, mixed, and transfected for 4 hours at 37° C. and 110 rpm, in 5% $CO_2$. Equal volume of pre-warmed SFX4HEK293 medium was added after 4 hours, and then 100 μg/ml GENETICIN aminoglycoside antibiotic was added and incubated at 37° C. and 130 rpm, in 5% $CO_2$ for 10 days. The supernatant was directly collected for purification or the supernatant was collected and stored at −80° C.

1.2.d. PEI-mediated co-transfection of HEK293-E cells with two expression vectors of portion B antibody constructed in 1.1.d. The cells were cultured in SFX4HEK293 medium (HYCLONE) and GIBCO FREESTYLE 293 medium in a ratio of 1:1 to which 100 μg/ml GENETICIN aminoglycoside antibiotic was added, and the cells were diluted to 1.5-2.5×$10^6$ cells/ml with fresh medium one day before transfection and incubated at 37° C. and 120 rpm in 5% $CO_2$ for transfection on the following day. Taking a 1 L shaking flask (CORNING) as an example, the cells were collected by centrifugation at 1000 rpm for 5 min on the following day, and then washed once with 50 ml GIBCO FREESTYLE 293 medium. The cells were collected by centrifugation at 1000 rpm for 5 min, and then resuspended in 150 ml GIBCO FREESTYLE 293 medium to a cell density of 4×$10^6$ cells/ml in a new 1 L shaking flask (CORNING). Plasmids for co-transfection were used in an amount of 0.5 μg DNA per $10^6$ cells at equimolar ratio of the vectors of genes encoding various chains, and the DNAs were diluted with GIBCO FREESTYLE 293 medium to (40 ng/μL). DNA: PEI (polyscience cationic transfection reagent)=1:3 were added to the uniformly mixed DNAs and incubated for 20 min at room temperature. The cell suspension was added, mixed, and transfected for 4 hours at 37° C. and 110 rpm, in 5% $CO_2$. Equal volume of pre-warmed SFX4HEK293 medium was added after 4 hours, and then 100 μg/ml GENETICIN aminoglycoside antibiotic was added and incubated at 37° C. and 130 rpm, in 5% $CO_2$ for 10 days. The supernatant was directly collected for purification or the supernatant was collected and stored at −80° C.

1.3. Protein L Affinity Purification of Antibody in Fermentation Liquor

The protein was purified from the filtered cell culture supernatant following a standard procedure. Briefly, the antibody was load to protein L affinity chromatography (GE HEALTHCARE) and washed with PBS (containing 20 mM phosphate, 150 mM NaCl pH 6.8-7.4). The impurity components were washed off with 100 mM citrate buffer at pH 5.0, and the antibody was eluted with 100 mM citrate buffer at pH 3.0, and then immediately neutralized with 1 M tris-Hcl buffer at pH 9.0. A portion of the sample was provided for subsequent protein analysis by for example, SDS-PAGE. The monomeric antibody components were pooled for subsequent in-vitro ram splicing mediated by the intein. If necessary, the monomeric antibody components were concentrated using the MILLIPORE AMICON ULTRA (30 MWCO) centrifugal concentrator, frozen and stored at −20° C. or −80° C.

1.3.c. Protein L affinity purification of antibody in cell fermentation liquor obtained in Step 1.2.a: Protein L affinity purification of portion A antibody in fermentation liquor co-transfected with three expression vectors—The protein was purified from the filtered cell culture supernatant following a standard procedure. The supernatant from which the cells were filtered off was mixed with PBS (containing 20 mM phosphate, and 150 mM NaCl pH 6.8-7.4), flow through a Protein L affinity chromatographic column pre-equilibrated with PBS, and washed with PBS after loading. The impurity components were washed off with 100 mM citrate buffer at pH 5.0, and the antibody was eluted with 100 mM citrate buffer at pH 3.0, and then immediately neutralized with 1 M tris-Hcl buffer at pH 9.0. A portion of the sample was provided for subsequent protein analysis by, for example, SDS-PAGE. As shown in (FIG. 14), in the non-reduced sample, assembled portion A antibody of the bispecific antibody appears at around 103 KD. In the reducing electrophoresis, the heavy chain of 55 KD, the IC +Fc chain of 40 KD, and the light chain of 25 KD appear. The monomeric antibody component was pooled, which might be purified to obtain a purified product comprising mainly portion A antibody for subsequent in-vitro trans-splicing mediated by the intein. If necessary, the monomeric antibody components were concentrated using the MILLIPORE AMICON ULTRA (30 MWCO) ultrafiltration centrifuge tube, frozen and stored at −20° C. or −80° C.

1.3.b. Protein L affinity purification of antibody in cell fermentation liquor obtained in Step 1.2.b: Protein L affinity purification of portion A antibody in fermentation liquor co-transfected with three expression vectors—The protein was purified from the filtered cell culture supernatant following a standard procedure. The supernatant from which the cells were filtered off was mixed with PBS (containing 20 mM phosphate, and 150 mM NaCl pH 6.8-7.4), flow through a Protein L affinity chromatographic column pre-equilibrated with PBS, and washed with PBS after loading. The impurity components were washed off with 100 mM citrate buffer at pH 5.0, and the antibody was elated with 100 mM citrate buffer at pH 3.0, and then immediately neutralized with 1 M tris-Hcl buffer at pH 9.0. A portion of the sample was provided for subsequent protein analysis by, for example, SDS-PAGE. As shown in (FIG. 14), in the non-reduced sample, assembled portion A antibody of the bispecific antibody appears at around 103 KD. In the reducing electrophoresis, the heavy chain of 55 KD, the IC +Fc chain of 40 KD, and the light chain of 25 KD appear. The monomeric antibody component was pooled, which might be purified to obtain a purified product comprising mainly portion A antibody for subsequent in-vitro trans-splicing mediated by the intein. If necessary, the monomeric antibody components were concentrated using the MILLIPORE AMICON ULTRA (30 MWCO) ultrafiltration centrifuge tube, frozen and stored at −20° C. or −80° C.

1.3.c. Protein L affinity purification of antibody in cell fermentation liquor obtained in Step 1.2.c. The protein was purified from the filtered cell culture supernatant following a standard procedure. The supernatant from which the cells were filtered off was mixed with PBS (containing 2.0 mM phosphate, and 150 mM NaCl pH 6.8-7.4), flow through a Protein L affinity chromatographic column pre-equilibrated with PBS, and washed with PBS after loading. The impurity components were washed off with 100 mM citrate buffer at pH 5.0, and the antibody was eluted with 100 mM citrate buffer at pH 3.0, and then immediately neutralized with 1 M tris-Hcl buffer at pH 9.0. A portion of the sample was provided for subsequent protein analysis by, for example, SDS-PAGE. As shown in (FIG. 15), in the non-reduced sample, assembled portion B antibody of the bispecific antibody appears at around 60 KB. In the reduced sample, the VH+CH1+IN of 35 KD and the light chain of 25 KD appear. The monomeric antibody component was pooled, which might be purified to obtain a purified product comprising mainly portion B antibody for subsequent in-vitro trans-splicing mediated by the intein. If necessary, the monomeric antibody components were concentrated using the MILLIPORE AMICON ULTRA (30 MWCO) ultrafiltration centrifuge tube, frozen and stored at −20° C. or −80° C.

1.3.d. Protein L affinity purification of antibody in cell fermentation liquor obtained in Step 1.2.d. The protein was purified from the filtered cell culture supernatant following a standard procedure. The supernatant from which the cells were filtered off was mixed with PBS (containing 20 mM phosphate, and 1.50 mM to pH 6.8-7.4), flow through a Protein L affinity chromatographic column pre-equilibrated with PBS, and washed with PBS after loading. The impurity components were washed off with 100 mM citrate buffer at pH 5.0, and the antibody was eluted with 100 mM citrate buffer at pH 3.0, and then immediately neutralized with 1 M tris-Hcl buffer at pH 9.0. A portion of the sample was provided for subsequent protein analysis by, for example, SDS-PAGE. As shown in (FIG. 15), in the non-reduced sample, assembled portion B antibody of the bispecific antibody appears at around 60 KD. In the reduced sample, the VH+CH1+IN of 35 KD and the light chain of 25 KD appear. The monomeric antibody component was pooled, which might be purified to obtain a purified product comprising mainly portion B antibody for subsequent in-vitro trans-splicing mediated by the intein. If necessary, the monomeric antibody components were concentrated using the MILLIPORE AMICON ULTRA (30 MWCO) ultrafiltration centrifuge tube, frozen and stored at −20° C. or −80° C.

1.4. In-Vitro Trans-Splicing Mediated by the Split Intein of the Portions A and B As shown (in FIGS. 16 and 17), the portion A and B antibodies purified in Step 3 were mixed at a molar ratio of 1:1, and 0.05 mM to 2 mM DTT or β-mercaptoethanol was added. As shown in (FIG. 18), the final concentration of DTT is 0.01 mM, 0.05 mM, 1 mM, and 2 mM respectively. The results show that DTT can induce the occurrence of split intein-mediated trans-splicing at a concentration of 0.05 mM, and an obvious band of the bispecific antibody appears at 150 KD. Trans-splicing mediated by the split intein was induced to occur by a mercapto compound such as TCEP. 1 mM DTT or TCEP was added to the splicing reaction system at 4-37° C., and incubate respectively at 4, 22, and 37° C. As shown (in FIG. 19), the reaction occurs at 4° C., the reaction efficiency is higher at 22 and 37° C., and an obvious band of the bispecific antibody appears at 150 KD. 1 mM DTT was added to the splicing reaction system, and stood at 37° C. for 5 min, 15 min, 30 min, 60 min, and 120 min, respectively. As shown in (FIG. 20), a bispecific antibody is produced at 5 min, and the reaction reaches a plateau at 60 min. At the end of the reaction, the sulfhydryl compound needed to be removed, and the sulfhydryl compound could be removed by adding an oxidizing agent such as hydrogen peroxide, or removed by dialysis. Further, the mercapto compound might be diluted to below a working concentration by high-fold dilution with a buffer to achieve the purpose of terminating the reaction. The reaction was terminated and a sample was taken for detection by non-reducing SDS-PAGE.

Figure 21:
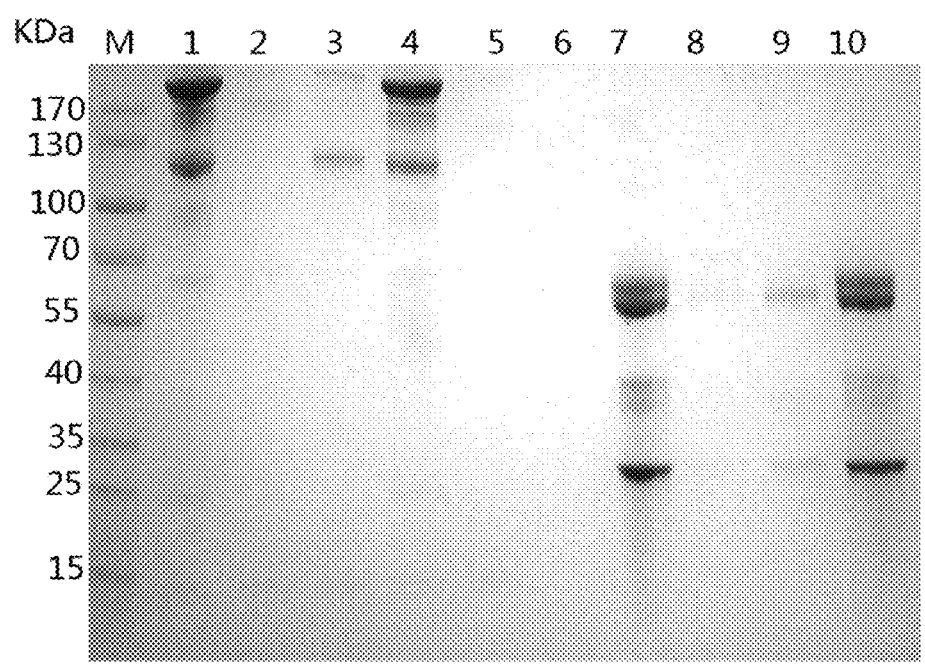
FIG. 21 is a SDS-PAGE electrophoretogram of a bispecific antibody purified by ProteinA affinity chromatography.

1.5. Protein a Purification of Product Obtained after Trans-Splicing Mediated by Split Intein of Portions A and B The protein was purified from the reaction mixture of Step 4 following a standard procedure. The sample was mixed with PBS (containing 20 mM phosphate, and 150 mM NaCl pH 6.8-7.4), run through a Protein A affinity chromatographic column pre-equilibrated with PBS, and washed with PBS after loading. The impurity component were washed off with 100 mM citrate buffer at pH 5.0, and the antibody was eluted with 100 mM citrate buffer at pH 3.0, and then immediately neutralized with 1 M tris-Hcl buffer at pH 9.0. A portion of the sample was provided for subsequent protein analysis by, for example, SIDS PAGE, as shown in (FIG. 21). FIG. 21 shows Coomassie blue staining of the product eluate from rProteinA chromatography in SDS-PAGE, in which M. marker; 1. before loading (N); 2. eluate from Ni column (N); 3. eluate 1 from rProteinA chromatography (N); 4. eluate 2 from rProteinA chromatography (N); 5. eluate 3 from rProteinA chromatography; 6. empty; 7. before loading (R); 8. eluate from Ni column (R); 9. eluate 1 from rProteinA chromatography (R) 10. eluate 2 from rProteinA chromatography (R), where N denote Nonreduciug, and R denote Reducing. It can be known from FIG. 21, in the non-reduced sample, an obvious band of a bispecific antibody formed by trans-splicing mediated by the split intein appears at 150 KD and the purity is high. In the reduced sample, only a heavy chain of about 50 KD and a light chain of about 25 KD appear. The monomeric antibody component was pooled. If necessary, the monomeric antibody component was concentrated using the MILLIPORE AMICON ULTRA (30 MWCO) ultrafiltration centrifuge tube, frozen and stored at −20° C. or −80° C.; or purified by, for example, ion exchange chromatography, hydrophobic chromatography, and molecular exclusion chromatography, to achieve a higher purity.

In summary, in the present disclosure, in order to solve the problem of mispairing of heavy chains, "Knob-into-Hole" is introduced, the VH and CH1 regions of one heavy chain are removed, and IC (C-fragment of the split intein) is fused to the N-hinge region of CH2. Thus, the heavy-chain homodimer component formed by the heavy chain that cannot be purified and removed is completely prevented. In order to introduce the "Knob-into-Hole" structure, (threonine) at position 366 in a CH3 region is mutated to W (tryptophan) to form a "Knob" structure. T (threonine) at position 366 in a CH3 region of another heavy chain is mutated to S (serine), L (leucine) at position 368 is mutated to A (alanine), and Y (tyrosine) at position 407 is mutated to V (valine), to form a "Hole" structure. In addition, in order to enhance the binding stability of the CH3 regions, S (serine) at position 354 of the "Knob" chain is mutated to C (cysteine), and Y (tyrosine) at position 349 on the "Hole" chain is mutated to C (cysteine) to enhance the stability between heavy chains by introducing a pair of inter-heavy chain disulfide bonds. Also, more importantly, an intact "Knob" heavy chain and "Hole" Fc chain are co-expressed. Due to the high difference in the properties of the "Knob" heavy chain homodimer and the "Hole" Fc homodimer from the target product, a heterodimer of the "Knob" heavy chain and the "Hole" Fc, separation and purification can be carried out simply. Therefore, the problem of mispairing of heavy chains can be completely avoided in the final product.

In the present disclosure, a bispecific antibody is split into an antigen A binding portion and an antigen B binding portion for the first time, as shown (in FIGS. 2 and 3), which are expressed separately, and then ligated into a intact antibody by protein trans-splicing by a split intein. The two light chains do not exist at the same time, and the two VH+CH1 chains do not exist at the same time, so there is no case where the light chain of A binds to the heavy chain of B, either the case where the light chain of B binds to A. Therefore, the situation of mispairing of light chains is avoided completely.

In the present disclosure, the trans-splicing function of the split intein is combined with the construction of bispecific antibodies for the first time, and portion A and B antibodies expressed and purified separately are linked to form an intact antibody by means of the am-splicing function of the split intein. This kind of specific antibodies is similar in structure to naturally occurring antibody molecules, thereby avoiding the instability of antibody molecules due to structural differences and the high immunogenicity in vivo.

In the present disclosure, recombinant gene expression technology is used to produce a bispecific antibody, and the sequence used may be a humanized antibody sequence or a fully human antibody sequence, to finally obtain a humanized or fully human bispecific antibody. This will greatly reduce the immunogenicity of the bispecific antibody in vivo, laying a foundation for the use of the bispecific as a drug.

Since the portion A antibody retains the entire Fc region, the bispecific antibody obtained by trans-splicing mediated by the intein also retains the entire Fc region, thus retaining the effector functions of the antibody, such as complement-dependent cytotoxicity (CDC) or antibody dependent cellular cytotoxicity (ADCC) and extended half-life of binding to FcRn (Fc receptor) in vascular endothelium.

In the present disclosure, both portion A and B antibodies are expressed in a mammalian cell expression system, for example, by transiently transfecting 293E, 293F, or CHO cells, and stably transfecting CHO cells. The products expressed by mammalian cells are glycosylated and more similar in structure to natural antibody molecules. The bispecific antibodies obtained by intein-mediated trans-splicing are well glycosylated and have well maintained stability of the bispecific antibody molecules, and antibody effects such as ADCC, CDC, etc., the in vivo half-life is prolonged, and the duration of the effect of action of the drug is increased.

In the method for preparing a bispecific antibody according to the present disclosure, the purification process is easy and convenient in operation. First, both portions A and B can be recovered by chromatography with a high recovery rate, such as ProteinL or ProteinA/G affinity chromatography. The bispecific antibody obtained by intein-mediated trans-splicing can be recovered by chromatography with a high recovery rate, such as ProteinA/G affinity chromatography, which can facilitate the subsequent hydrophobic chromatography, or ion exchange chromatography, and other operations. Therefore, the difficulty of purification is greatly reduced and a high-quality product can be obtained.

Since the hinge region between CH1 and CH2 of the antibody heavy chain is flexible and the primary Fab region in the Fc region of the antibody is substantially identical in structure, the method is applicable to the production of any bispecific antibodies with no need to perform property analysis based on the nature of each antibody. The present disclosure is fully applicable to the production of bispecific antibodies of any of the antibody subtypes (IgG, IgA, IgM, IgD, IgE, IgM, and light chain kappa and lambda), thus having broad universality.

Specific embodiments of the present disclosure are described above. It should be understood that the present disclosure is not limited to the above specific embodiments, and various variations or modifications can be made by those skilled in the art without departing from the scope of the claims, which do not affect the essence of the present disclosure.

What is claimed is:

1. A method for expressing and preparing a bivalent bispecific antibody, the bivalent bispecific antibody comprising a first light chain and a first heavy chain of an antibody that specifically binds to a first antigen, and a second light chain and a second heavy chain of an antibody that specifically binds to a second antigen, the method comprising:

S1: providing a first polynucleotide sequence and a second polynucleotide sequence, wherein the first polynucleotide sequence encodes a portion A antibody, wherein the second polynucleotide sequence encodes a portion B antibody, wherein the portion A antibody comprises the first light chain, the first heavy chain, an Fc chain of the second heavy chain, a part A of a hinge of the second heavy chain linked to the N-terminus of the Fc chain of the second heavy chain and a C-terminal fragment of a split intein (Ic) fused to the N terminus of then part A of the hinge of the second heavy chain, wherein the portion B antibody comprises the second light chain a VH+CH1 chain of the second heavy chain, a part B of the hinge of the second heavy chain linked to the C-terminus of the VH+CH1 chain of the second heavy chain, and a N-terminal fragment of the split intein (In) fused to the C terminus of the part B of the hinge of the second heavy chain, and S2: constructing a first mammalian cell expression vector and a second mammalian cell expression vector, wherein the first mammalian cell expression vector comprises the first polynucleotide sequence and is configured to express the portion A antibody, and the second mammalian cell expression vector comprises the second polynucleotide sequence and is configured to express the portion B antibody;

S3: transfecting a first mammalian cell with the first mammalian expression vector, and inducing the first mammalian cell transfected with the first mammalian cell expression vector to express the portion A antibody; and transfecting a second mammalian cell with the second mammalian expression vector, and inducing the second mammalian cell transfected with the second mammalian cell expression vector to express the portion B antibody; and S4: purifying the expressed portion A antibody and the expressed portion B antibody respectively, and subjecting the Ic of the portion A antibody and the In of the portion B antibody to trans-splicing in vitro, to obtain the bivalent bispecific antibody, wherein the trans-splicing, in vitro, occurs at a temperature of 4-37° C., is continued for 5-20 min, and the concentration of the sulfhydryl compound is 0.05-2 mM and the split intein is Npu DNA E or Ssp DnaE, wherein the Fc chain of the second heavy chain in portion A antibody is fused to the VH+CH1 chain of the second heavy chain in portion B antibody by the Ic/In linkage of the part A of the hinge and the part B of the hinge of the second heavy chain, and wherein the part A of hinge is one portion of the hinge region of the antibody, the part B of hinge is another portion of said hinge region of the antibody, and part A and part B are fused to a whole of said hinge region after trans-splicing of the intein in S4.

2. The method for expressing and preparing a bivalent bispecific antibody according to claim 1, wherein the bivalent bispecific antibody comprises a knob-in-hole structure with a knob formed at a CH3 domain in the first heavy chain and a hole formed at a CH3 domain in the second heavy chain.

3. The method for expressing and preparing a bivalent bispecific antibody according to claim 2, wherein the threonine at position 366 in the CH3 domain of the first heavy chain is mutated to tryptophan to form the knob; and in the CH3 domain of the second heavy chain, the threonine at position 366 is mutated to serine, the leucine at position 368 is mutated to alanine, and the tyrosine at position 407 is mutated to valine, to form the hole.

4. The method for expressing and preparing a bivalent bispecific antibody according to claim 3, wherein the serine at position 354 in the CH3 domain of the first heavy chain is mutated to cysteine; and the tyrosine at position 349 in the CH3 domain of the second heavy chain is mutated to cysteine.

5. The method for expressing and preparing a bivalent bispecific antibody according to claim 1, wherein the bivalent bispecific antibody comprises a knob-in-hole structure with a hole formed at a CH3 domain in the first heavy chain and a knob formed at a CH3 domain in the second heavy chain.

6. The method for expressing and preparing a bivalent bispecific antibody according to claim 5, wherein in the CH3 domain of the first heavy chain, the threonine at position 366 is mutated to serine, the leucine at position 368 is mutated to alanine, and the tyrosine at position 407 is mutated to valine, to form the hole; and wherein in the CH3 domain of the second heavy chain, the threonine at position 366 is mutated to tryptophan, to form the knob.

7. The method for expressing and preparing a bivalent bispecific antibody according to claim 6, wherein in the CH3 domain of the first heavy chain, the tyrosine at position 349 is mutated to cysteine; and in the CH3 domain of the second heavy chain, the serine at position 354 is mutated to cysteine.

8. The method for expressing and preparing a bivalent bispecific antibody according to claim 1, wherein the transfection of mammalian cells is transient transfection of 293-E, 293-F or CHO cells, or stable transfection of CHO cells.

9. The method for expressing and preparing a bivalent bispecific antibody according to claim 1, further comprising: terminating the trans-splicing reaction and purifying the product obtained after trans-splicing, in vitro, to obtain the bivalent bispecific antibody.

10. The method for expressing and preparing a bivalent bispecific antibody according to claim 1, wherein the sulfhydryl compound comprises DTT, β-mercaptoethanol and/or TCEP.

* * * * *